United States Patent
Tam et al.

(10) Patent No.: US 8,119,606 B2
(45) Date of Patent: Feb. 21, 2012

(54) CRYSTALLINE D-ISOGLUTAMYL-D-TRYPTOPHAN AND THE MONO AMMONIUM SALT OF D-ISOGLUTAMYL-D-TRYPTOPHAN

(75) Inventors: Tim Fat Tam, Vaughan (CA); Blaise N'Zemba, Brampton (CA); Regis Leung-Tuong, Mississuaga (CA); Yingsheng Wang, Toronto (CA); Yanqing Zhao, Toronto (CA); Lily Yu, Woodbridge (CA)

(73) Assignee: Apotex Technologies, Toronto (CA)

( * ) Notice: Subject to any disclaimer, the term of this patent is extended or adjusted under 35 U.S.C. 154(b) by 404 days.

(21) Appl. No.: 12/515,217

(22) PCT Filed: Nov. 26, 2007

(86) PCT No.: PCT/CA2007/002123
§ 371 (c)(1),
(2), (4) Date: May 15, 2009

(87) PCT Pub. No.: WO2008/064465
PCT Pub. Date: Jun. 5, 2008

(65) Prior Publication Data
US 2010/0016243 A1   Jan. 21, 2010

(30) Foreign Application Priority Data
Nov. 28, 2006   (CA) .................................. 2569204

(51) Int. Cl.
*A61K 38/05* (2006.01)
(52) U.S. Cl. .................................................. 514/21.91
(58) Field of Classification Search .................. None
See application file for complete search history.

(56) References Cited

U.S. PATENT DOCUMENTS

| | | | |
|---|---|---|---|
| 5,736,519 | A | 4/1998 | Deigin et al. |
| 5,744,452 | A | 4/1998 | Kobolov et al. |
| 5,902,790 | A | 5/1999 | Green et al. |
| 5,916,878 | A | 6/1999 | Kolobov et al. |
| 6,103,699 | A | 8/2000 | Deigin et al. |
| 6,410,515 | B1 | 6/2002 | Deigin et al. |

FOREIGN PATENT DOCUMENTS

| | | |
|---|---|---|
| DE | 3400603 | 7/1985 |
| WO | WO 98/54351 | 12/1998 |
| WO | WO 99/33799 | 7/1999 |

OTHER PUBLICATIONS

Iyo, Hiromi et al.; Sequence-dependent interaction of acidic amino acid with guanine base in tryptophane containing dipeptides: spectroscopic studies, Chemical and Pharmaceutical Bulletin, 1991, vol. 39, pp. 2483-2486.
Kashirin, D.M., et al. (2000); Pharmaceutical Chemistry Journal, 34(11), 619-622, "The Use of IR Spectroscopy for the Identification of Synthetic Peptide Preparations—Thyogen, Thymodepressing and Neogen".
Korotky, N.G. et al, Clinical potential of thymodepressin in patients with psoriasis and mechanism of its therapeutic action, Vestnik Dermatologii i Veneralogii, 2002, N. 4; pp. 58-60.
Low, M. et al.; 1978, Hoppe-Seyler's Z. Physiol. Chem., 359(12); 1643-51, "Tert-Butylation of the Tryptophan Indole Ring".
Marder, O., and Alberico, F.; Jun. 2003; Chemical Oggi (Chemisty Today), 6-32, "Industrial application of coupling reagents in peptides".
Pandit, U.K.; 1989, Pure & Appl. Chem., vol. 61, No. 3., pp. 423-426, "Synthetic Studies on sesbanimides".
Sapuntsova, S.G. et al.; May 2002; Bulletin of Experimental Biology and Medicine, 133(5), 488-490, "Proliferative Process in the Epidermis of Patients with Atopic Dermatitis Treated with Thymodepressin".
Schmidbaur, Hubert et al., Potassium hudrogen L-glutamate monohydrate K(L-GIuH), H20, Chemische Berichte, 1990, vol. 123, pp. 1001-1004.
Semina, O.V., et al; Effects of iEW synthetic peptide isomers on bone marrow colony-forming capacity in vivo, Bulletin of Experimental Biology and Medicine, 2005, vol. 140, pp. 348-351.
Tkacheva, A., et al.; 2004, Eksp Klin Gastroenterol (6):29-33, 163, "Impact of Bestin on Immunological Status".
Wiesbrock, Frank et al, Lithium L-hydrogen alpha glutamate: a layer structure with asymmetrical tunnels formed by nets with two difference macrocycles, Cryst. Eng. Comm. 2003, vol. 5, pp. 262-264.

*Primary Examiner* — Christina Bradley

(57) ABSTRACT

A process for making pure crystalline D-isoglutamyl-D-tryptophan is provided which includes the step of deprotecting essentially pure N-tert-butoxycarbonyl-D-isoglutamyl-D-tryptophan or its diester to yield essentially pure D-isoglutamyl-D-tryptophan. A process is also provided for the preparation of pure mono ammonium salt of D-isoglutamyl-D-tryptophan from essentially pure N-tert-butoxycarbonyl-D-isoglutamyl-D-tryptophan. D-isoglutamyl-D-tryptophan, ammonium salt (1:1) is a stable pharmaceutical solid.

6 Claims, 8 Drawing Sheets

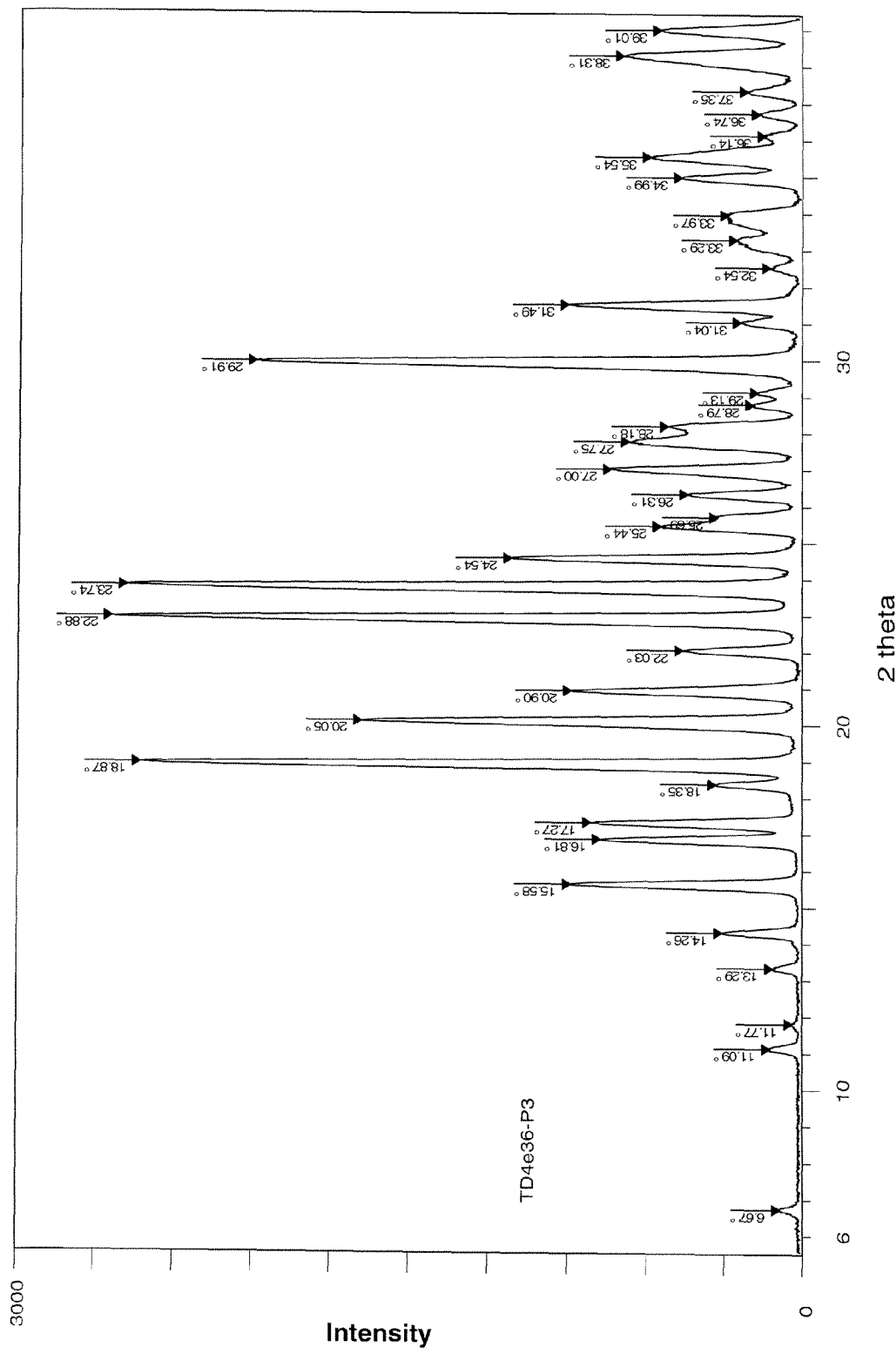
Figure 1: Powder X-ray Diffraction Pattern of crystalline D-isoglutamyl-D-tryptophan
Reference no. TD4e36-P3

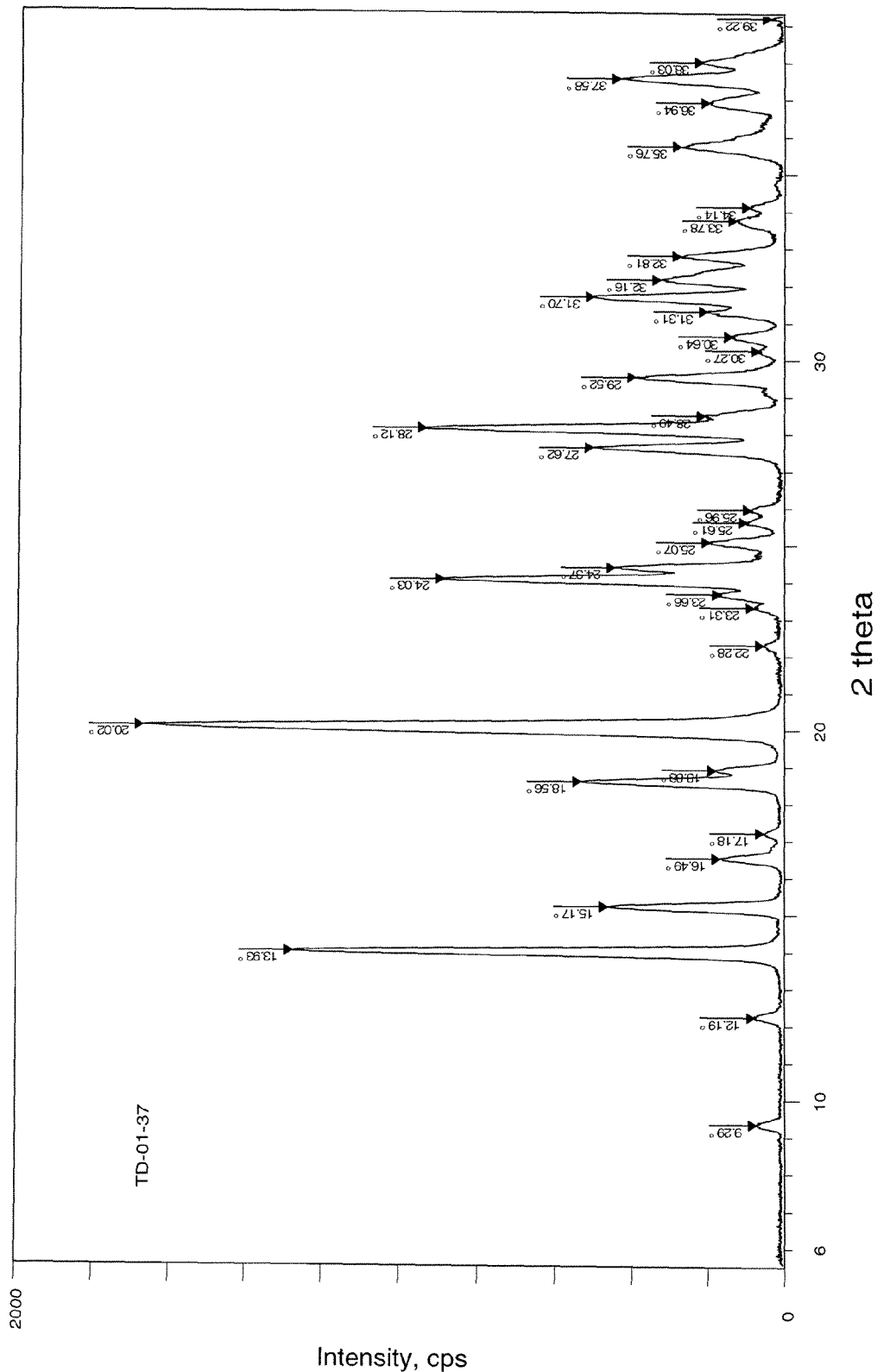
Figure 2: Powder X-ray Diffraction Pattern of Mono Ammonium salt of D-isoglutamyl-D-tryptophan
Reference No. TD-01-37

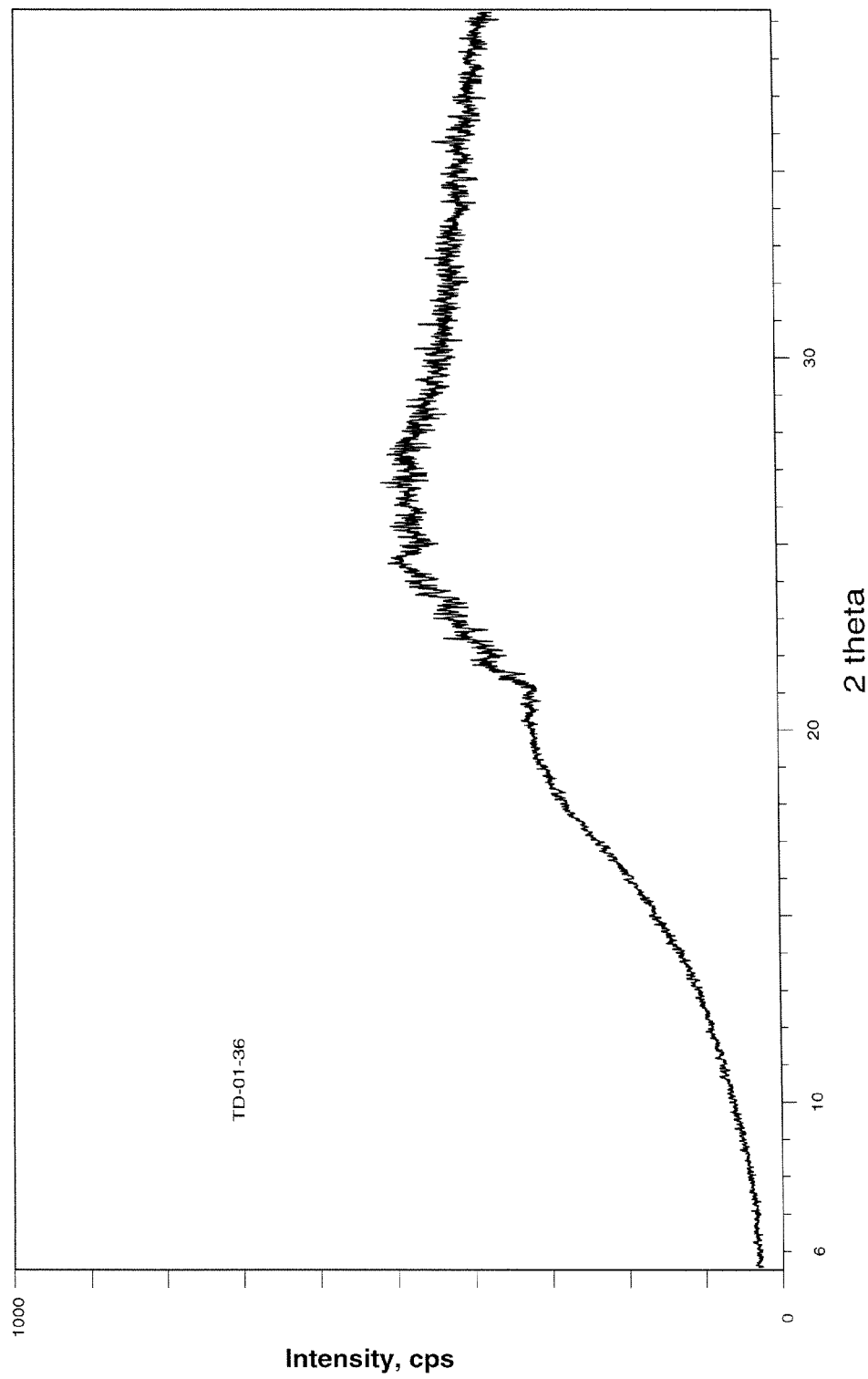
Fig. 3: Powder X-ray Diffraction Pattern of Amorphous Mono ammonium salt of D-isoglutamyl-D-tryptophan
Reference No. TD-01-36

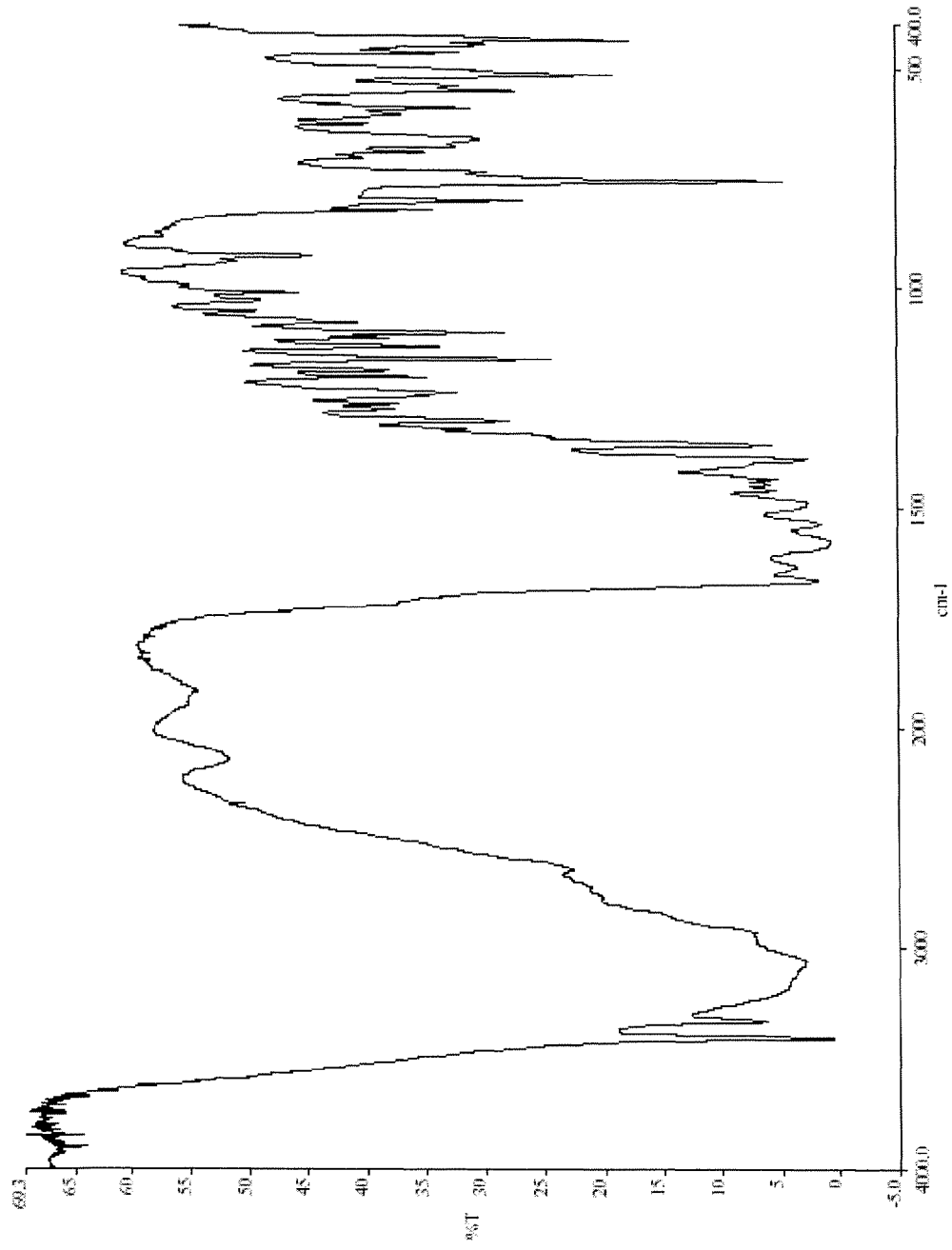
Figure 4: FTIR of crystalline mono ammonium salt of D-isoglutamyl-D-tryptophan

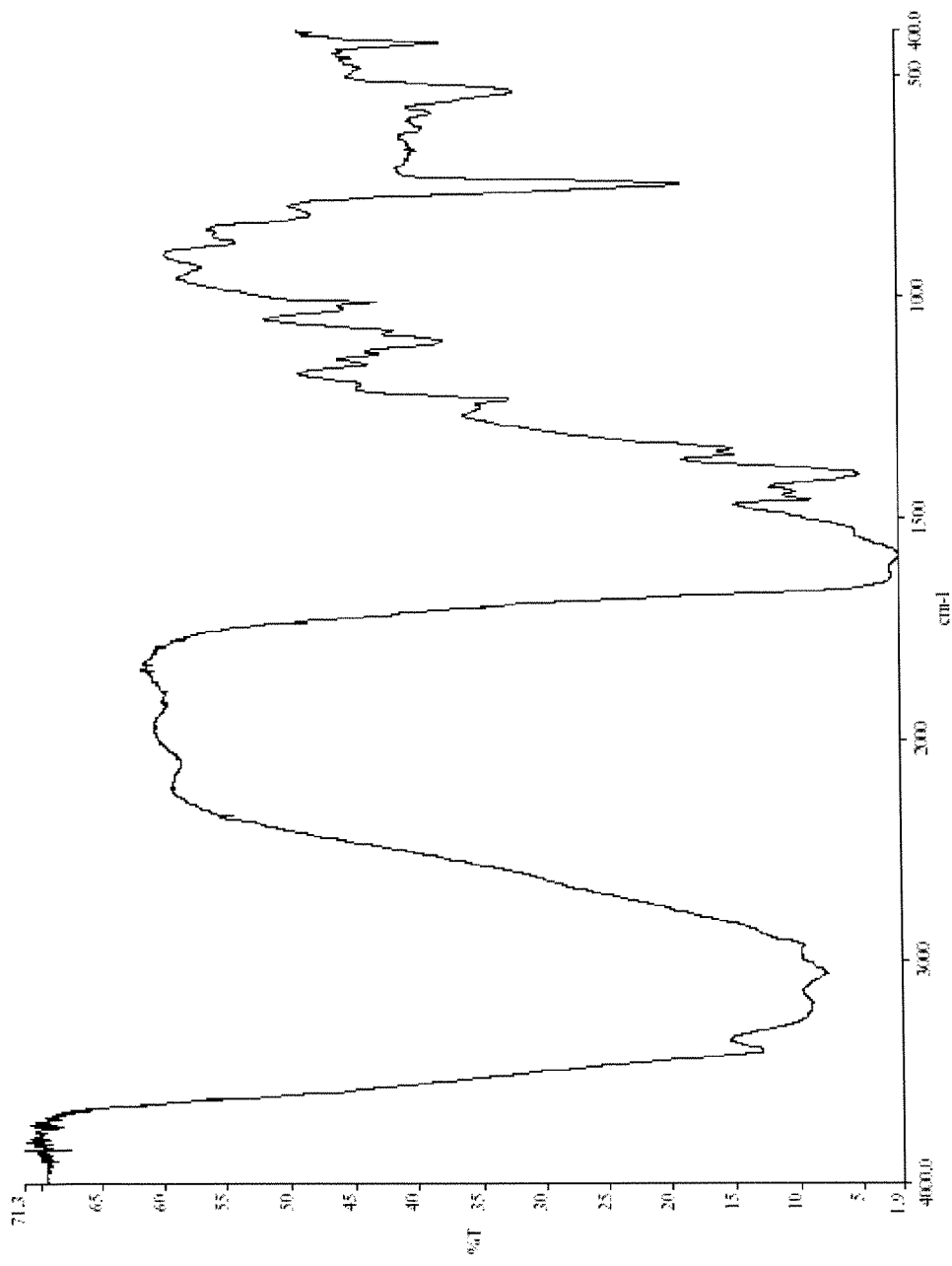

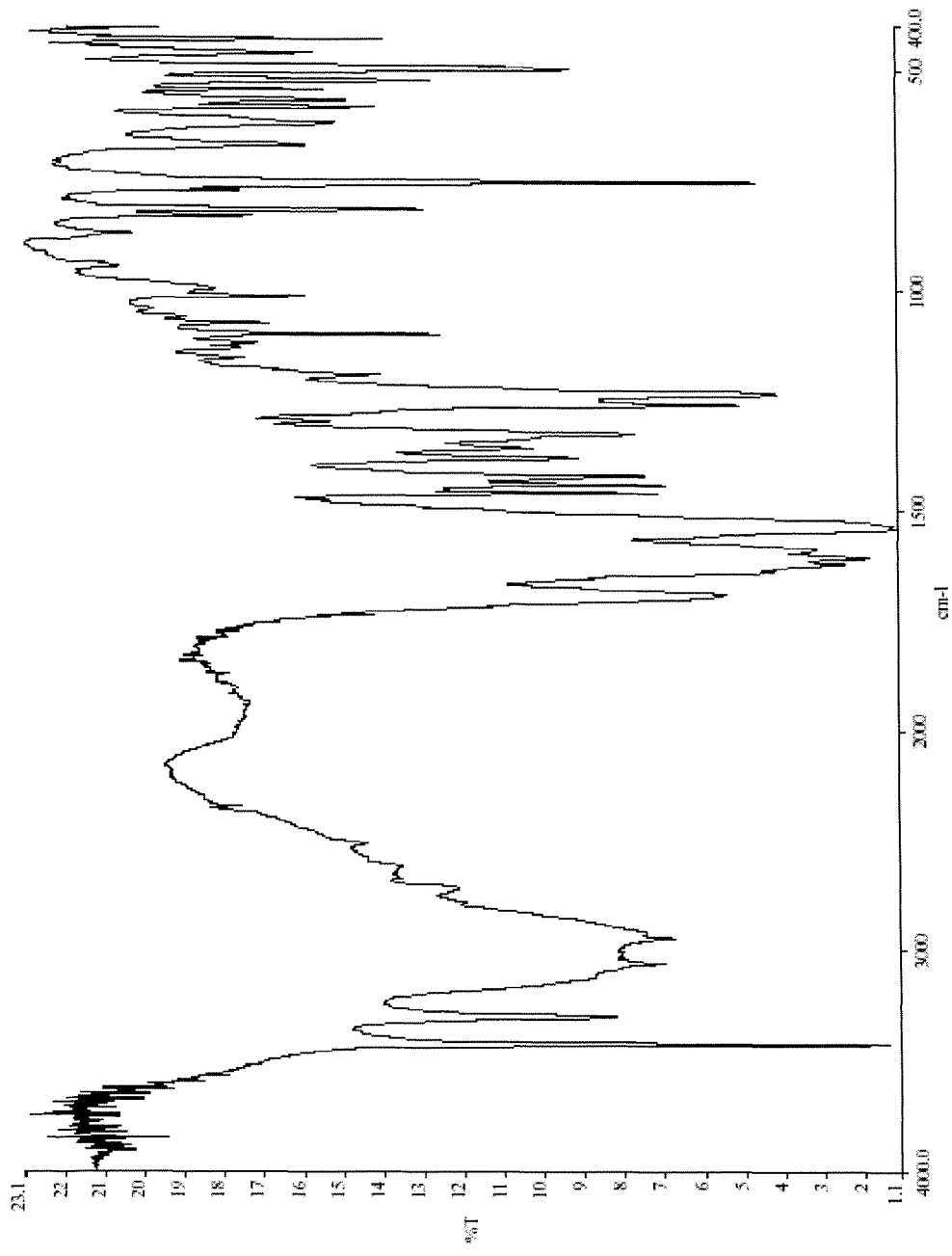
Figure 6 is a characteristic infrared (IR) absorption spectrum of D-isoglutamyl-D-tryptophan.

Fig. 7: Speciation plot of thymodepressin using estimated pKas and the software Hyperquad Simulation & Speciation.
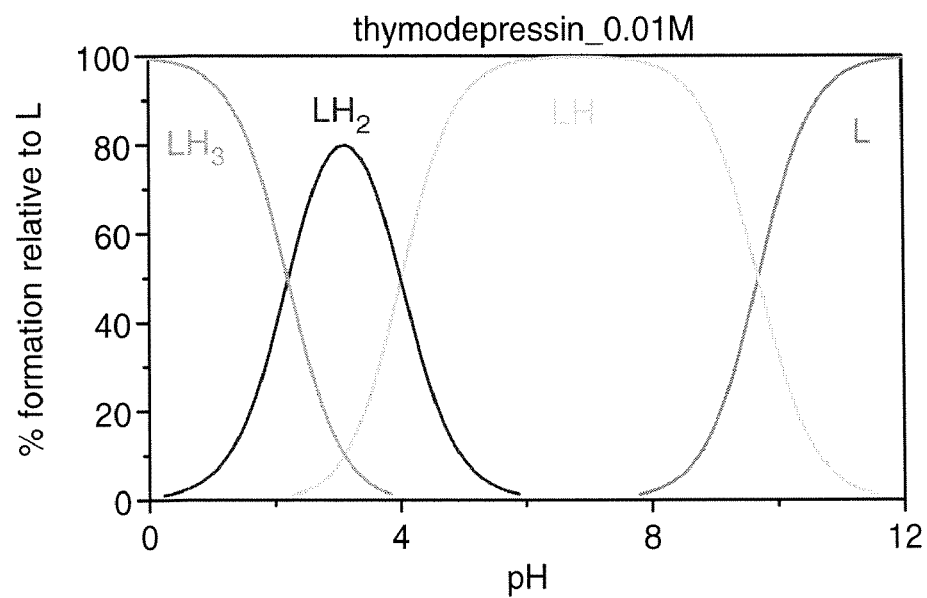

Fig. 8: Speciation plot of thymodepressin using experimentally determined pKas and the software Hyperquad Simulation & Speciation.
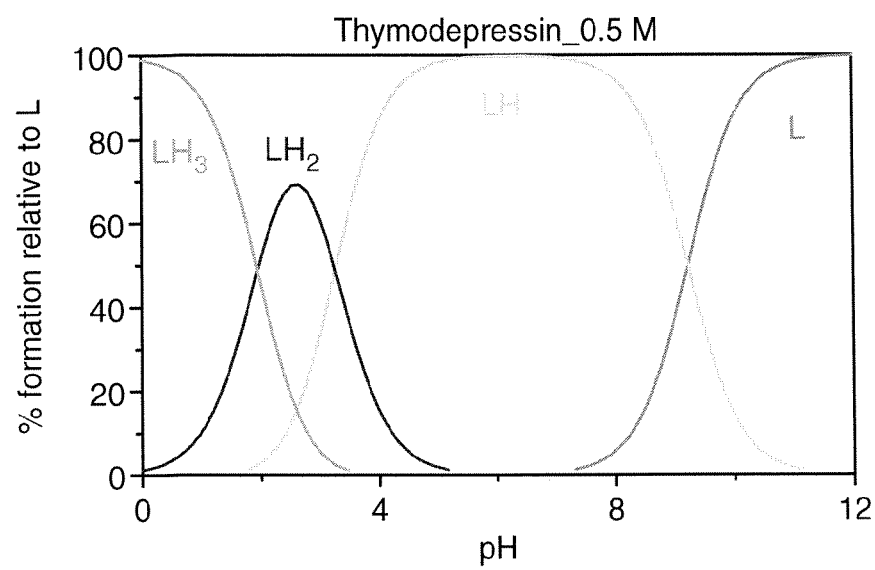

CRYSTALLINE D-ISOGLUTAMYL-D-TRYPTOPHAN AND THE MONO AMMONIUM SALT OF D-ISOGLUTAMYL-D-TRYPTOPHAN

FIELD OF THE INVENTION

The present invention relates to a novel stable crystalline form of D-isoglutamyl-D-tryptophan, and a process for its isolation in pure form, free from inorganic salts. The present invention also relates to a novel stable ammonium salt of D-isoglutamyl-D-tryptophan, and a process for its production in pure form by crystallization and/or traditional silica gel column chromatography.

BACKGROUND OF THE INVENTION

D-isoglutamyl-D-tryptophan (also known as H-D-iGlu-Trp-OH or Thymodepressin) is a synthetic hemoregulatory dipeptide developed for the treatment of autoimmune diseases including psoriasis (Sapuntsova, S. G., et al. (May 2002), Bulletin of Experimental Biology and Medicine, 133 (5), 488-490). Thymodepressin is considered an effective treatment for psoriasis in Russia (U.S. Pat. No. 5,736,519), where the drug is currently sold as the disodium salt in liquid formulation for injection and intranasal administration. It is an immunosuppressant and selectively inhibits proliferation of bone marrow cells and thus induces immune depression.

The known solid form of D-isoglutamyl-D-tryptophan disodium salt is an amorphous powder which is hygroscopic and very difficult to handle. The structure of thymodepressin disodium salt is described in Kashirin, D. M., et al. (2000), Pharmaceutical Chemistry Journal, 34(11), 619-622. The mono sodium salt of D-isoglutamyl-D-tryptophan is identified by the Chemical Abstracts Service (CAS) Registry System and is listed in the CAS REGISTRY[SM] File, but there is no publication concerning its preparation and physical properties. A powdery or amorphous form of a compound such as D-isoglutamyl-D-tryptophan, intended for pharmaceutical use may give rise to manufacturing problems due to bulk density issues, hygroscopicity and variable water content that cannot be corrected by vacuum drying. D-isoglutamyl-D-tryptophan is a dipeptide and the drying of an amorphous form at elevated temperature, for example, 80-100° C. under vacuum is not recommended.

The only synthesis of H-D-iGlu-D-Trp-OH reported in the literature is disclosed in U.S. Pat. No. 5,736,519. According to the process reported in Example 1 of U.S. Pat. No. 5,736,519, which is depicted herein as Scheme 1, Boc-D-Glu-OH (1.1) is reacted with 1,3-dicyclohexylcarbodiimide (DCC) to give the cyclic anhydride (1.2). Upon removal of the dicyclohexyl urea (DCU) by filtration, the anhydride (1.2) is reacted with H-D-Trp-OH to give a mixture of the dipeptide Boc-D-iGlu-D-Trp-OH (1.3) and Boc-D-Glu-D-Trp-OH (1.4). The yield of the combined crude Boc-D-iGlu-D-Trp-OH (1.3) and Boc-D-Glu-D-Trp-OH (1.4) is 70%. However, the mixture only contains no more than 35% of the desired intermediate Boc-D-iGlu-D-Trp-OH (1.3). The Boc protective group is removed by stirring a solution of the (1.3) and (1.4) in formic acid as the solvent at 40° C. for 1 hr. The ratio of (1.3) and (1.4) to formic acid is about 1 g:8 mL (weight to volume). The product is a mixture of H-D-iGlu-D-Trp-OH (1.5) and H-D-Glu-D-Trp-OH (1.6). Since the peptides (1.5) and (1.6) are present in equal amount, the purification requires ion exchange chromatography using pyridine acetate buffer. The yield of the desired product H-D-iGlu-D-Trp-OH (1.5) is 35% from Boc-D-iGlu-D-Trp-OH (1.3). Thus, the overall yield of H-D-iGlu-D-Trp-OH (1.5) from Boc-D-Glu-OH is 12.25%.

Scheme 1: Synthesis of H-D-iGlu-D-Trp-OH as described in U.S. Pat. No. 5,736,519.

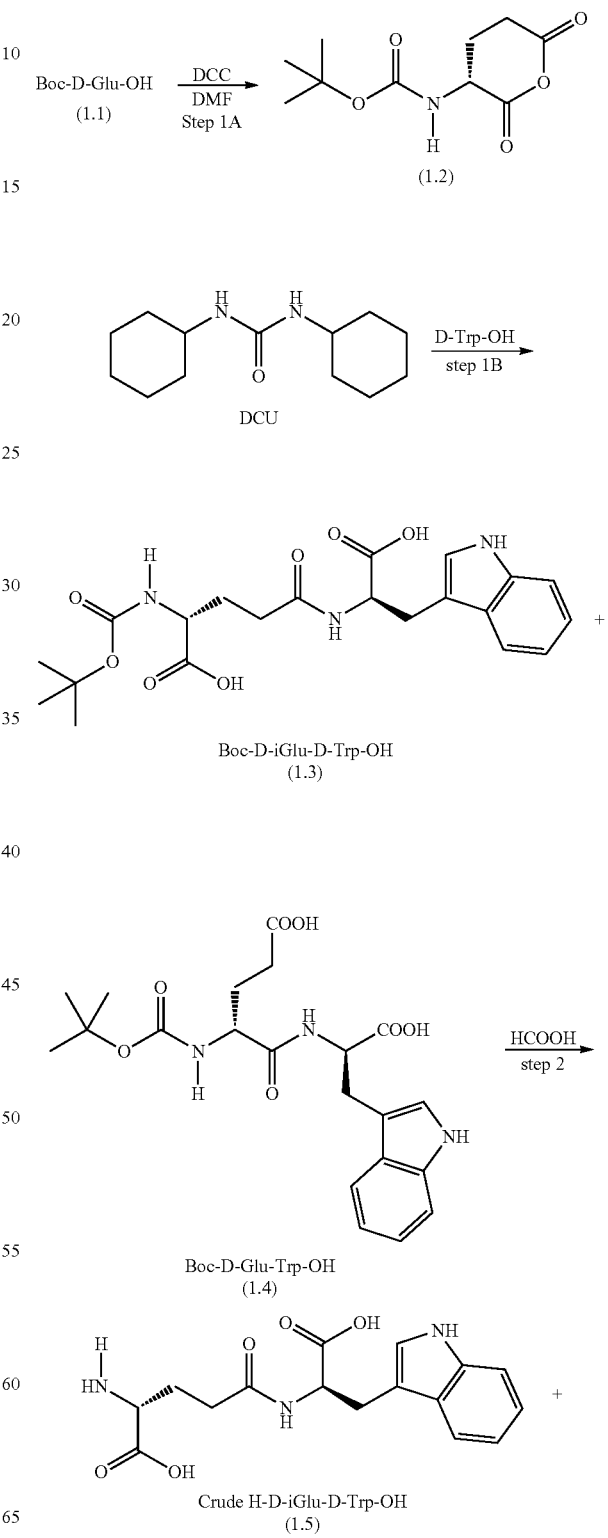

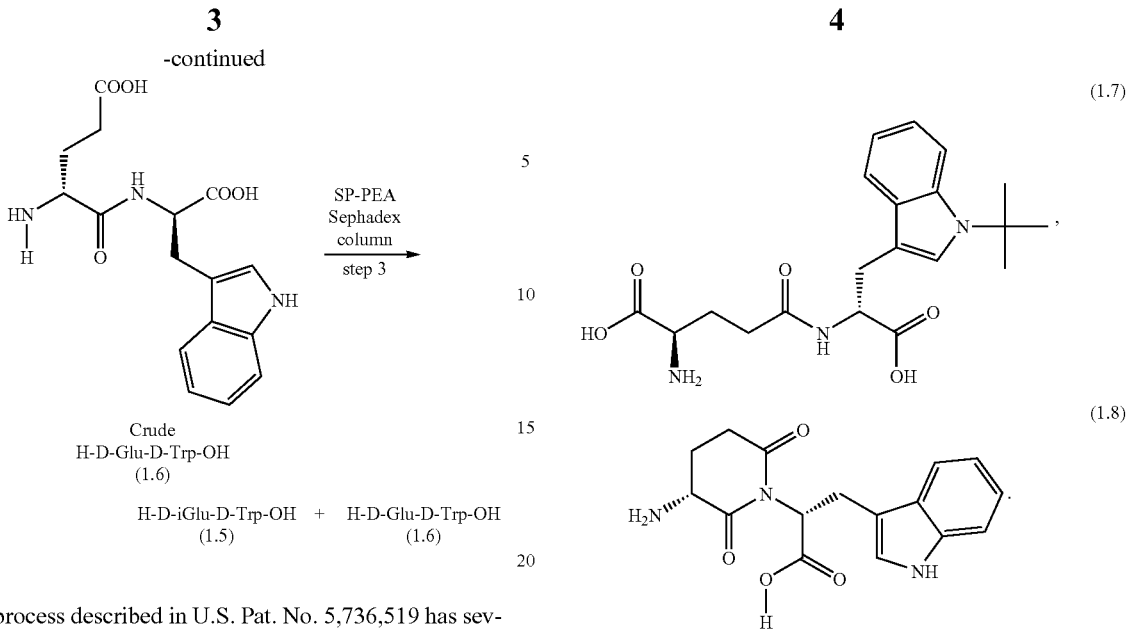

Crude
H-D-Glu-D-Trp-OH
(1.6)

H-D-iGlu-D-Trp-OH + H-D-Glu-D-Trp-OH
(1.5)                       (1.6)

The process described in U.S. Pat. No. 5,736,519 has several disadvantages as follows:

1. DCC in step 1A may lead to other by-products such as

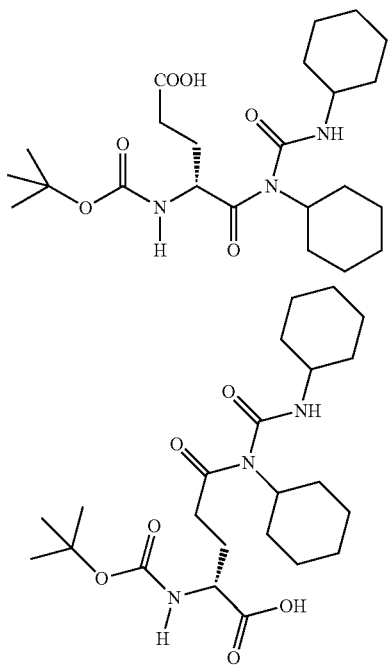

The by-products from DCC coupling of peptides have been reported in Marder, O., and Albericio, F. (June 2003), Chemical Oggi (Chemistry Today), 6-32.

2. The deprotection of Boc-D-iGlu-D-Trp-OH (1.3) requires elevated temperature and the final purification of H-D-iGlu-D-Trp-OH requires a very toxic solvent pyridine. Elevated temperature in the deprotection of (1.3) may result in the N-tert-butyl indole derivative (1.7) as an impurity (Löw, M., et. al. (1978), Hoppe-Seyler's Z. Physiol. Chem., 359(12):1643-51). In addition, the peptide may cyclize to give the glutarimide (1.8) (Pandit, U.K. (1989), Pure & Appl. Chem., Vol. 61, No. 3, pp. 423-426).

3. The coupling reaction only produces a 1:1 mixture of Boc-D-iGlu-D-Trp-OH (1.3) and Boc-D-Glu-D-Trp-OH (1.4). The maximum yield of (1.3) cannot exceed 50% in the coupling step 1B. A mixture of D-Glu-D-Trp-OH and D-iGlu-D-Trp-OH is formed at the end of the synthesis. The peptides must be separated by ion exchange chromatography and reverse phase preparative high pressure liquid chromatography. The overall yield of H-D-iGlu-D-Trp-OH (1.5) is 12.25% and preparative HPLC purification is very time consuming and inefficient. The retention time for two similar isomers H-D-iGlu-D-Trp-OH (1.5) and H-D-Glu-D-Trp-OH (1.6) are not reported. Repeated cycles of separation to enrich the purity of the desired isomer (1.5) are very inefficient. This process cannot be amenable to the large scale manufacturing.

4. The opposite diastereomer L-isoglutamyl-L-tryptophan (also known as H-L-iGlu-L-Trp-OH or Bestim) is an immunostimulant (see U.S. Pat. No. 5,774,452). Bestim has been used in ulcer treatment. It decreases the inflammatory effect in the stomach and duodenal mucosa and precipitates regress of clinical symptoms and scarring of the ulcer (Tkacheva, A., et al. (2004), Eksp Klin Gastroenterol. (6):29-33, 163). The synthesis of the H-L-iGlu-L-Trp-OH, mono sodium salt (1:1) is depicted in Scheme 2 (U.S. Pat. No. 5,744,452).

Scheme 2: Synthesis of [L-iGlu-L-Trp-O⁻] Na⁺ as described in U.S. Pat. No. 5,744,452.

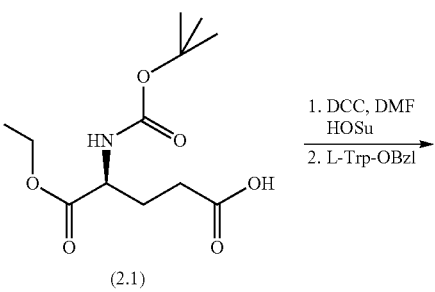

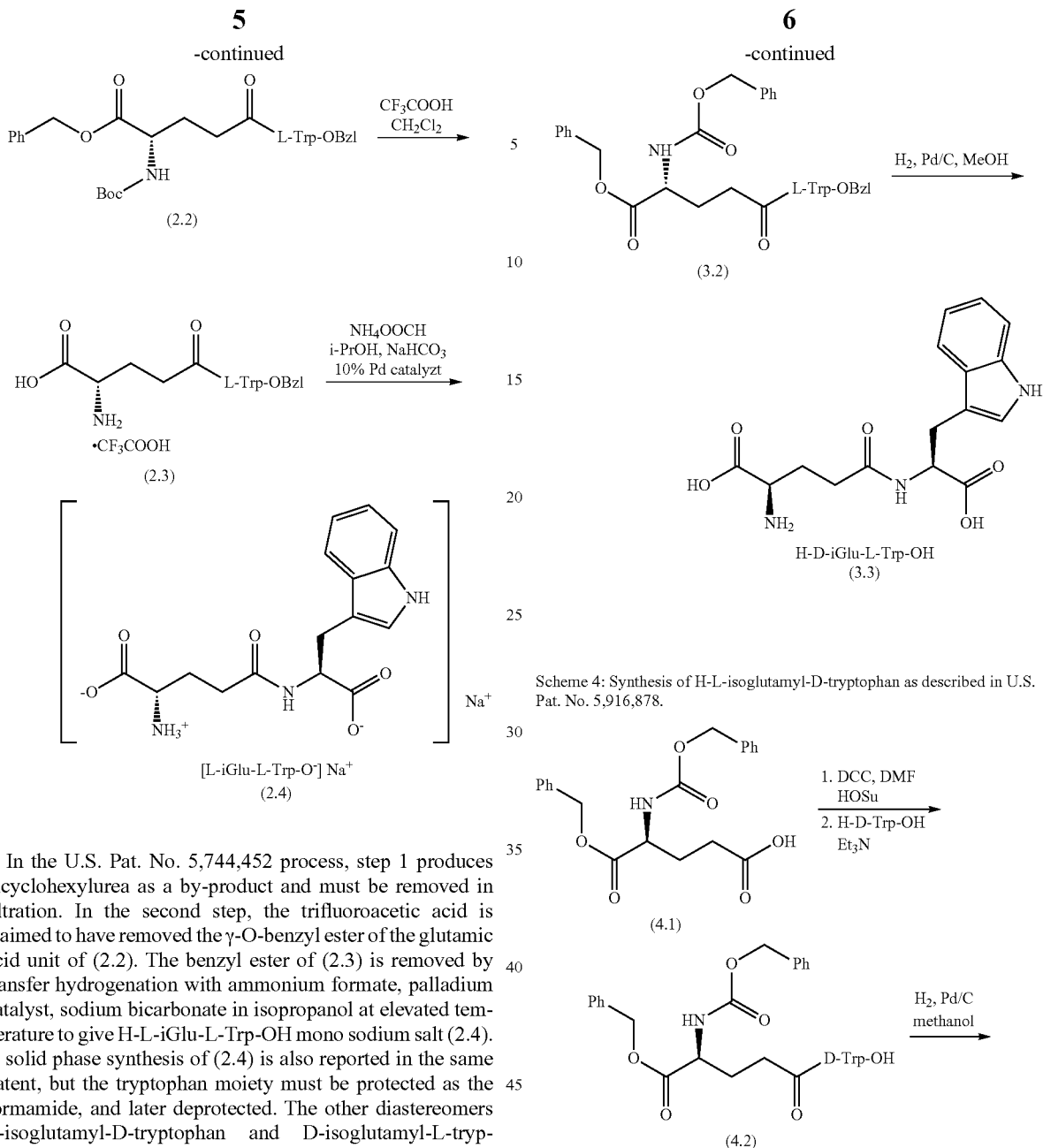

In the U.S. Pat. No. 5,744,452 process, step 1 produces dicyclohexylurea as a by-product and must be removed in filtration. In the second step, the trifluoroacetic acid is claimed to have removed the γ-O-benzyl ester of the glutamic acid unit of (2.2). The benzyl ester of (2.3) is removed by transfer hydrogenation with ammonium formate, palladium catalyst, sodium bicarbonate in isopropanol at elevated temperature to give H-L-iGlu-L-Trp-OH mono sodium salt (2.4). A solid phase synthesis of (2.4) is also reported in the same patent, but the tryptophan moiety must be protected as the formamide, and later deprotected. The other diastereomers L-isoglutamyl-D-tryptophan and D-isoglutamyl-L-tryptophan are also known compounds (U.S. Pat. No. 5,916,878).

The syntheses of the H-D-iGlu-L-Trp-OH and H-L-iGlu-D-Trp-OH are reported in Scheme 3 and Scheme 4, respectively (U.S. Pat. No. 5,916,878).

Scheme 3: Synthesis of H-D-isoglutamyl-L-tryptophan as described in U.S. Pat. No. 5,916,878.

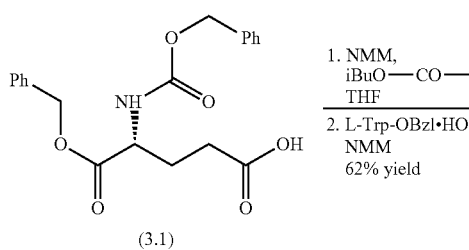

The processes reported in Schemes 2, 3 and 4 may have overcome the regiospecific synthesis of gamma amide product (2.2), (3.2) and (4.2) without the formation of the alpha amide product, but they involve a hydrogenation step in the removal of a benzyl ester in compounds (2.3), (3.2) and (4.2).

This requires the use of a large amount of palladium catalyst. The second concern is the partial reduction of the indole ring at the manufacturing scale. The third concern is the formation of glutarimide, 2-(3-amino-2,6-dioxo-piperidin-1-yl)-3-(1H-indol-3-yl)-propionic acid in the hydrogenation process. The fourth concern is cost. The cost of a CBz-Glu-OBzl derivative such as (3.1) and (4.1) is almost twice the price of the corresponding Boc-Glu-OBzl in fine chemicals manufacturing. The processes in schemes 3 and 4 require HPLC purification of the final product. The overall yields are 33% and 35.9%, respectively. Scheme 2 requires the use of trifluoroacetic acid, which introduces other impurities into the reaction. Furthermore, the process in Scheme 2 uses dicyclohexylcarbodiimide as a peptide coupling agent. The removal of trace amount of impurities from this reagent is a serious issue in chemical manufacturing. The technology is therefore not amenable to industrial production, and the same cannot be adopted for the large scale production of H-D-isoglutamyl-D-tryptophan.

SUMMARY OF THE INVENTION

The present invention relates to a novel stable crystalline form of D-isoglutamyl-D-tryptophan, and a process for isolation of the said compound in pure form, free from inorganic salts, by precipitation from water, without reverse phase preparative high pressure liquid chromatography. A process is reported for the preparation of pure N-tert-butoxycarbonyl-D-isoglutamyl-D-tryptophan and its diester, free of N-tert-butoxycarbonyl-D-glutamyl-D-tryptophan, and the conversion of N-tert-butoxycarbonyl-D-isoglutamyl-D-tryptophan and its diester into the pure crystalline D-isoglutamyl-D-tryptophan. The novel crystalline D-isoglutamyl-D-tryptophan of present invention is easy to purify. When compared to the prior art processes described above, the present invention provides a number of advantages as follows:

First, D-isoglutamyl-D-tryptophan is prepared in crystalline form without preparative high pressure liquid chromatography.

Second, the key intermediate Boc-D-iGlu-D-Trp-OH or H-D-Glu-(γ-D-Trp-OMe)-α-OBzl HCl salt is prepared in high yield and high purity.

Third, a process is provided for the conversion of Boc-D-iGlu-D-Trp-OH and its diester or H-D-Glu-(γ-D-Trp-OMe)-α-OBzl HCl salt to D-isoglutamyl-D-tryptophan in high yield and high purity.

Fourth, the pure crystalline form of D-isoglutamyl-D-tryptophan of the present invention is unknown in the prior art. It can be used directly in liquid formulation with pH adjustment, thus eliminating the need for the use of the extremely hygroscopic and unstable disodium salt of D-isoglutamyl-D-tryptophan.

The present invention also relates to a novel stable ammonium salt of D-isoglutamyl-D-tryptophan, and a process for the production of the same from N-tert-butoxycarbonyl-D-isoglutamyl-D-tryptophan and isolating such compound in pure form by crystallization and/or traditional silica gel column chromatography.

The mono ammonium salt of D-isoglutamyl-D-tryptophan is a stable solid and is easy to dispense for formulation purposes. A speciation plot is provided to identify the salt form species at different pH.

The novel process for the manufacture of D-isoglutamyl-D-tryptophan and its D-isoglutamyl-D-tryptophan, ammonium salt (1:1) circumvents the above described manufacturing problems and renders possible the recovery and work-up of the thymodepressin and thymodepressin mono ammonium salt in traditional chemical process equipment.

It is an object of the present invention to provide a good manufacturing process for D-isoglutamyl-D-tryptophan resulting in the drug material being completely free of the other diastereomers as discussed above and the ability of the material to be stored in a stable form for a prolonged period before it is formulated.

It is another object of the present invention to provide the D-isoglutamyl-D-tryptophan free of the alpha amide isomer D-glutamyl-D-tryptophan.

It is a further object of the present invention to provide a process for preparing pure D-isoglutamyl-D-tryptophan (H-D-iGlu-D-Trp-OH) from the acid addition salt of H-D-iGlu-D-Trp-OH which results in a product which is essentially or entirely free of organic solvent residues, and does not require reverse phase high pressure liquid chromatography purification. The solid D-isoglutamyl-D-tryptophan is isolated from water.

It is a further object of the present invention to provide a process for preparing pure D-isoglutamyl-D-tryptophan (H-D-iGlu-D-Trp-OH) from the base addition salt of H-D-iGlu-D-Trp-OH which results in a product which is essentially or entirely free of organic solvent residues, and does not require reverse phase high pressure liquid chromatography purification. The solid D-isoglutamyl-D-tryptophan is isolated from water.

It is a further object of the present invention to provide a process which produces D-isoglutamyl-D-tryptophan which is essentially free of inorganic salt contaminants.

It is a further object of the present invention to produce crystalline D-isoglutamyl-D-tryptophan having an X-ray powder diffraction (XRPD) pattern as shown in FIG. 1.

It is a further object of the present invention to produce D-isoglutamyl-D-tryptophan mono ammonium salt from the acid addition salt of D-isoglutamyl-D-tryptophan which results in a product which is essentially or entirely free of organic solvent residues, and does not require reverse phase high pressure liquid chromatography purification. The solid D-isoglutamyl-D-tryptophan ammonium salt is isolated from isopropanol and ammonia after treatment with ion exchange resin to remove inorganic salts.

It is a further object of the invention to produce D-isoglutamyl-D-tryptophan mono ammonium salt having an XRPD pattern as shown in FIG. 2.

It is a further object of the present invention to produce amorphous D-isoglutamyl-D-tryptophan mono ammonium salt characterized essentially by the Fourier Transform Infrared (FTIR) spectrum as shown in FIG. 5.

It is a further object of the present invention to provide a process which produces D-isoglutamyl-D-tryptophan mono ammonium salt which is essentially free of inorganic salt contaminants.

It is a further object of the present invention to provide a process for the manufacture of an acid addition salt of H-D-iGlu-D-Trp-OH, in particular the hydrochloride salt, from pure Boc-D-iGlu-D-Trp-OH.

It is a further object of the present invention to provide a process for the manufacture of pure dipeptide Boc-D-iGlu-D-Trp-OH without chromatography separation.

It is a further object of the present invention to provide a simple silica gel column chromatography separation method for the purification of D-isoglutamyl-D-tryptophan and its mono ammonium salt.

It is a further object of the present invention to provide a speciation plot to determine the pH range for the isolation of D-isoglutamyl-D-tryptophan and its mono monovalent salt.

The preferred pH range for the precipitation of D-isoglutamyl-D-tryptophan in water is from about 2.5 to about 3.0.

The acid addition salt of D-isoglutamyl-D-tryptophan derives from the dipeptide Boc-D-iGlu-D-Trp-OH, which is prepared from the base hydrolysis of the compound of formula I:

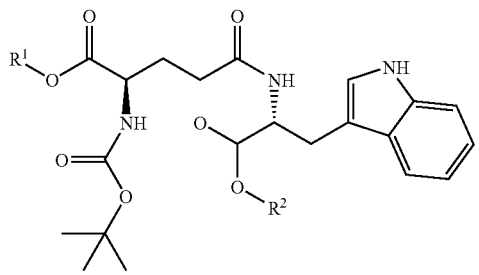

wherein $R^1$ is selected from the group consisting of $C_1$-$C_4$ alkyl and benzyl, and $R^2$ is $C_1$-$C_4$ alkyl, with the proviso that the $C_4$ alkyl is not tert-butyl,
with metal hydroxide in water and an inert solvent in the presence of methanol to give Boc-D-iGlu-D-Trp-OH, free from other diastereomers. The metal hydroxide is selected from the group consisting of lithium hydroxide, sodium hydroxide and potassium hydroxide.

The compound of formula I is in turn prepared from the peptide coupling of Boc-D-Glu(OH)—$OR^1$ and D-Trp-$OR^2$ wherein $R^1$ and $R^2$ is as defined above with the peptide coupling reagents such as HOBt and EDC. This method of synthesis of Boc-D-iGlu-D-Trp-OH offers significant advantages over the prior art in U.S. Pat. No. 5,736,519 because the product is exclusivity the gamma peptide product Boc-D-iGlu-D-Trp-OH and the alpha peptide product Boc-D-Glu-D-Trp-OH cannot be formed in the synthesis because Boc-D-Glu(OH)—$OR^1$ is used.

Acid deprotection of the pure dipeptide Boc-D-iGlu-D-Trp-OH with acid such as hydrochloric acid, trifluoroacetic acid affords the acid addition salt. A solution of the acid addition salt is adjusted to a pH of about 2.5 to about 3.0 to obtain the thymodepressin as a solid precipitate.

Alternatively, the acid addition salt can be converted to an ammonium salt by subjecting an aqueous solution of the material to ion exchange chromatography with sulfonic acid based resin. Upon removal of the salt with elution using water, the ion exchange resin is washed with ammonia and isopropanol mixture to obtain the crude ammonium salt, which recrystallizes from isopropanol and water to give the pure mono ammonium salt.

A solution of the base addition salt of D-isoglutamyl-D-tryptophan is prepared by the acid deprotection, in particular HCl deprotection, of a compound of formula I wherein each of $R^1$ and $R^2$ are independently selected from the group consisting of $C_1$-$C_4$ alkyl and benzyl to give the acid addition salt of the diester H-D-Glu-(γ-D-Trp-$OR^2$)-α-$OR^1$, which is then treated with a metal hydroxide in water and an inert solvent in the presence of methanol to give the base addition salt of H-D-iGlu-D-Trp-OH. The metal hydroxide is selected from the group consisting of sodium hydroxide, lithium hydroxide and potassium hydroxide. Extraction with a water immiscible solvent removes the organic impurity into the organic phase, and the aqueous phase is separated and adjusted to a pH of about 6 to about 7 with the metal hydroxide. After solvent evaporation to reduce the amount of solvent to an estimated ratio of solute to solvent in the ratio of less than about 1:8 wherein the solute is the peptide D-isoglutamyl-D-tryptophan in base addition salt form, this solution of base addition salt is adjusted to a pH of about 2.5 to about 3.0 with mineral acid to effect the precipitation of D-isoglutamyl-D-tryptophan.

Whilst it is not intended that the scope and operation of the present invention should be in any way limited by theory or by its mode of operation and possible explanations thereof, it is believed that at a pH of about 2.5 to about 3.0, the speciation plot in FIG. 7 and FIG. 8 showed that the main species of thymodepressin is the free peptide (H-D-iGlu-D-Trp-OH) and not the monovalent salt. Since H-D-iGlu-D-Trp-OH is not very soluble in organic solvent free water (solubility in water <23 mg per mL), the compound precipitates out of solution in pure form. The XRPD pattern of the material is shown in FIG. 1.

In the manufacturing of the mono ammonium salt, a solution of thymodepressin at a pH of about 6.0 to about 8.0 is purified by ion exchange to remove the salt. The ammonia based regenerant solution affords the pure mono ammonia salt after crystallization from isopropanol and water. Although one may speculate that the mono ammonium salt is unstable and may revert to the free dipeptide, in practice, the compound is in fact stable for more than two years. The present applicant has invented the mono ammonium salt of thymodepressin which is a stable, novel chemical entity that can easily be crystallized from isopropanol and water. The properties of the crystalline material obtained are shown in FIG. 2.

The above processes produce pure thymodepressin and mono ammonium salt without reverse phase HPLC on an industrial scale, but thymodepressin and mono ammonium salt can be purified by traditional silica gel column chromatography using the conditions as stated above. Therefore, instead of discarding any thymodepressin in the mother liquor from crystallization, the filtrate can be concentrated and further purified by silica gel column chromatography if so desired.

BRIEF DESCRIPTION OF THE DRAWINGS

The crystalline salts of the present invention are described in the Examples hereinafter.

FIG. 1 is a characteristic XRPD pattern of crystalline D-isoglutamyl-D-tryptophan. The XRPD pattern may also be expressed in terms of inter-planar distances d, Bragg's angle 2 theta, and relative intensity (expressed as a percentage with respect to the most intense ray) as follows:

| Angle [°2 theta] | d-value [Å] | Rel. Int [%] |
|---|---|---|
| 6.67 | 13.239 | 3 |
| 11.09 | 7.975 | 4.4 |
| 11.77 | 7.515 | 1.2 |
| 13.29 | 6.655 | 4 |
| 14.26 | 6.205 | 11.3 |
| 15.58 | 5.685 | 33.3 |
| 16.81 | 5.269 | 28.9 |
| 17.27 | 5.13 | 30.4 |
| 18.35 | 4.832 | 12.2 |
| 18.87 | 4.7 | 95.8 |
| 20.05 | 4.424 | 63.6 |
| 20.9 | 4.247 | 33.2 |
| 22.03 | 4.032 | 17.1 |

-continued

| Angle [°2 theta] | d-value [Å] | Rel. Int [%] |
|---|---|---|
| 22.88 | 3.884 | 100 |
| 23.74 | 3.744 | 97.9 |
| 24.54 | 3.625 | 41.9 |
| 25.44 | 3.499 | 20.3 |
| 25.69 | 3.465 | 12.1 |
| 26.31 | 3.384 | 16.4 |
| 27 | 3.3 | 27.4 |
| 27.75 | 3.212 | 24.9 |
| 28.18 | 3.164 | 19.3 |
| 28.79 | 3.099 | 6.8 |
| 29.13 | 3.063 | 6.2 |
| 29.91 | 2.985 | 79.2 |
| 31.04 | 2.879 | 8.6 |
| 31.49 | 2.839 | 33.7 |
| 32.54 | 2.749 | 4.4 |
| 33.29 | 2.689 | 9.3 |
| 33.97 | 2.637 | 10.5 |
| 34.99 | 2.562 | 17.3 |
| 35.54 | 2.524 | 21.8 |
| 36.14 | 2.483 | 5.1 |
| 36.74 | 2.444 | 5.9 |
| 37.35 | 2.406 | 7.7 |
| 38.31 | 2.348 | 25.6 |
| 39.01 | 2.307 | 20.3 |

The powdered samples were prepared by a normal front packing technique and run on a D8 Discovery Diffractometer system with Cu-kα source operating at 45 kV/45 mA. The system is equipped with 2D—proportional area detector (GADDS). The experimental data were collected on two frames at 600 s exposure of each one that covered the range of 3°-35° (2-theta). The obtained 2D diffraction images were then integrated in order to obtain standard, I vs. 2-theta, diffraction patterns. The data were processed by various Bruker AXS data processing software including: Eva™ 8.0 and Topas™ v. 2.1 (for profile fitting analysis and applications, when necessary).

FIG. 2 is a characteristic XRPD pattern of a crystalline mono ammonium salt of D-isoglutamyl-D-tryptophan. The XRPD pattern may also be expressed in terms of inter-planar distances d, Bragg's angle 2 theta, and relative intensity (expressed as a percentage with respect to the most intense ray) as follows:

| Angle [°2 theta] | d-value [Å] | Rel. Int [%] |
|---|---|---|
| 9.29 | 9.517 | 4.1 |
| 12.19 | 7.258 | 4.5 |
| 13.93 | 6.354 | 76.2 |
| 15.17 | 5.837 | 27.4 |
| 16.49 | 5.371 | 9.8 |
| 17.18 | 5.157 | 3 |
| 18.56 | 4.778 | 31.6 |
| 18.88 | 4.696 | 10.5 |
| 20.02 | 4.431 | 100 |
| 22.28 | 3.986 | 3 |
| 23.31 | 3.814 | 4.6 |
| 23.66 | 3.757 | 9.8 |
| 24.03 | 3.7 | 52.9 |
| 24.37 | 3.649 | 26.3 |
| 25.07 | 3.549 | 11.4 |
| 25.61 | 3.475 | 5.6 |
| 25.96 | 3.43 | 5 |
| 27.62 | 3.227 | 29.7 |
| 28.12 | 3.17 | 55.7 |
| 28.49 | 3.131 | 12.2 |
| 29.52 | 3.023 | 23.1 |
| 30.27 | 2.951 | 3.7 |

-continued

| Angle [°2 theta] | d-value [Å] | Rel. Int [%] |
|---|---|---|
| 30.64 | 2.915 | 7.9 |
| 31.31 | 2.854 | 11.8 |
| 31.7 | 2.821 | 29.6 |
| 32.16 | 2.781 | 19.2 |
| 32.81 | 2.728 | 16 |
| 33.78 | 2.652 | 7.4 |
| 34.14 | 2.625 | 5.1 |
| 35.76 | 2.509 | 16 |
| 36.94 | 2.431 | 11.6 |
| 37.58 | 2.391 | 25.6 |
| 38.03 | 2.364 | 12.5 |
| 39.22 | 2.295 | 1.9 |

The X-ray powder diffraction spectra for D-isoglutamyl-D-tryptophan and its ammonium salt above are shown in the FIG. 1 and FIG. 2 hereinafter. It will be understood that the 2-theta values of the X-ray powder diffraction pattern may vary slightly from one machine to another or from one sample to another, and so the values quoted are not to be construed as absolute.

FIG. 3 is a characteristic XRPD pattern of an amorphous form of D-isoglutamyl-D-tryptophan.

FIG. 4 is a characteristic infrared (IR) absorption spectrum of crystalline mono ammonium salt of D-isoglutamyl-D-tryptophan.

FIG. 5 is a characteristic infrared (IR) absorption spectrum of amorphous mono ammonium salt of D-isoglutamyl-D-tryptophan.

FIG. 6 is a characteristic infrared (IR) absorption spectrum of crystalline D-isoglutamyl-D-tryptophan.

FIG. 7 illustrates the speciation calculation of the dipeptide H-D-iGlu-D-Trp-OH and its salt using estimated pKas of the acid and amine groups. $LH_2$ is the diacid form of the peptide H-D-iGlu-D-Trp-OH, LH is the mono carboxylic acid salt of H-D-iGlu-D-Trp-OH. An example of such is the mono ammonium salt. L refers to the diacid salt form and one such example is the disodium salt of the peptide H-D-iGlu-D-Trp-OH.

FIG. 8 illustrates the speciation calculation of the dipeptide H-D-iGlu-D-Trp-OH and its salt using experimentally determined pKas of the acid and amine groups. $LH_2$ is the diacid form of the peptide H-D-iGlu-D-Trp-OH, LH is the mono carboxylic acid salt of H-D-iGlu-D-Trp-OH. An example of such is the mono ammonium salt. L refers to the diacid salt form and one such example is the disodium salt of the peptide H-D-iGlu-D-Trp-OH.

DETAILED DESCRIPTION OF THE INVENTION

As used herein, the term "Boc-D-Glu(OH)—$OR^1$" refers to the structure:

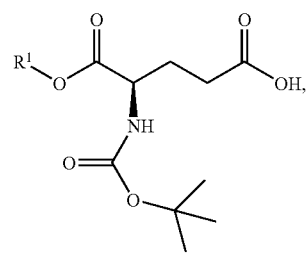

when R¹ is benzyl, it is the chemical 2-tert-butoxycarbonylamino-D-glutamic acid alpha-benzyl ester.

As used herein, the term "D-Trp-OR²" refers to the structure:

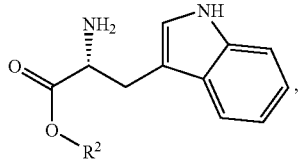

when R² is methyl, the compound is D-tryptophan methyl ester.

As used herein, the term "Boc-D-Glu-(γ-D-Trp-OR²)-α-OR¹" refers to the structure:

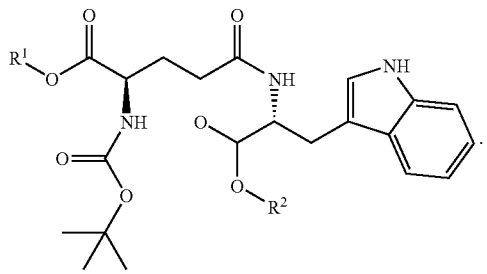

As used herein, the term "H-D-Glu-(γ-D-Trp-OR²)-α-OR¹" refers to the structure:

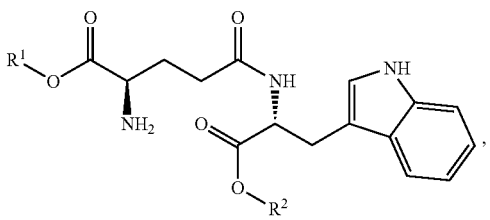

when R¹ is benzyl, R² is methyl, the compound is

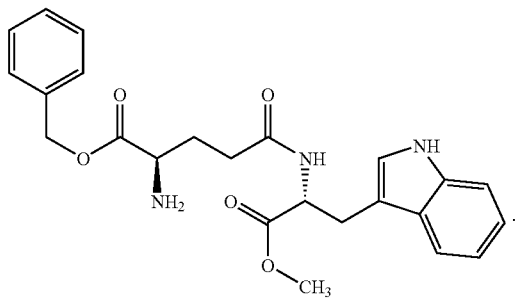

when R¹ is methyl, R² is methyl, the compound is

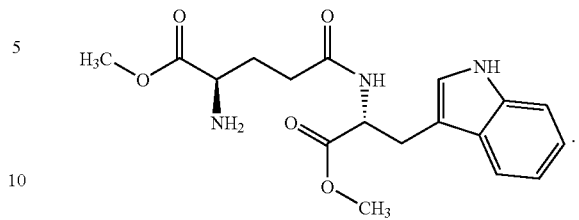

As used herein, the term "thymodepressin" refers to the dipeptide H-D-iGlu-D-Trp-OH with the chemical structure:

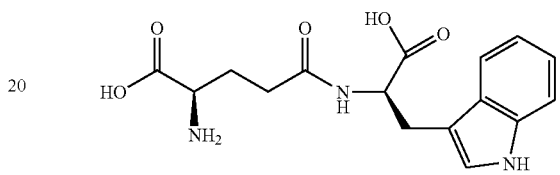

It can also be written as H-D-Glu-(γ-D-Trp-OH)—OH.

Acid addition salt is a salt formed after reacting the amine of H-D-iGlu-D-Trp-OH with inorganic acids including hydrochloric acid, sulphuric acid, hydrobromic acid, phosphoric acid, etc., or organic acids including formic acid, acetic acid, propionic acid, glycolic acid, lactic acid, pyruvic acid, oxalic acid, succinic acid, malic acid, tartaric acid, citric acid, trifluoroacetic acid, benzoic acid, salicylic acid, benzenesulphonic acid, and toluenesulphonic acids. It can also be formed from the acid deprotection of the Boc-D-iGlu-D-Trp-OH derivative.

Base addition salt is a salt formed from reacting the carboxylic acid of H-D-iGlu-D-Trp-OH with inorganic bases including sodium hydroxide, lithium hydroxide, potassium hydroxide, etc.

The present invention is directed to a process for the manufacture of H-D-iGlu-D-Trp-OH and its ammonium salt, free of inorganic salts, from the acid addition salts of H-D-iGlu-D-Trp-OH, which is preferably prepared from the dipeptide Boc-D-iGlu-D-Trp-OH. Boc-D-iGlu-D-Trp-OH is prepared from Boc-D-Glu(OH)—OR¹ and D-Trp-OR² wherein R¹ is selected from the group consisting of benzyl and $C_1$-$C_4$ alkyl and R² is $C_1$-$C_4$ alkyl with the proviso that $C_4$ alkyl is not tert-butyl.

The present invention is also directed to a process for the manufacture of H-D-iGlu-D-Trp-OH from a solution of the base addition salt of H-D-iGlu-D-Trp-OH, which is preferably prepared from the acid addition salt of the dipeptide H-D-Glu-(γ-D-Trp-OR²)-α-OR¹ wherein each of R¹ and R² is independently selected from the group consisting of benzyl and $C_1$-$C_4$ alkyl.

Preferred Embodiments

Within the several aspects of the present invention, which is set forth in the Summary of Invention, the sequence of process steps and their relative degrees of preference are described below:

In an embodiment of the present invention, there is provided an aqueous phase process for the preparation of H-D-iGlu-D-Trp-OH, free of inorganic salts, which comprises:

(a) preparing a solution of H-D-iGlu-D-Trp-OH acid addition salt in an aqueous medium essentially free of organic solvent; or preparing a solution of H-D-iGlu-D-Trp-OH base addition salt in an aqueous medium essentially free of organic solvent;

(b) adjusting the pH to the predominant pH for the diacid form with an alkali metal hydroxide solution or a mineral acid, to cause the precipitation of H-D-iGlu-D-Trp-OH;

(c) recovering the precipitated H-D-iGlu-D-Trp-OH thereof; and (d) vacuum drying the product resulting from step (c) to give H-D-iGlu-D-Trp-OH.

In another embodiment of the present invention, there is provided a crystalline form of H-D-iGlu-D-Trp-OH which is D-isoglutamyl-D-tryptophan that is characterized by the XRPD pattern expressed in the description of drawings.

In another embodiment of the present invention, there is provided the crystalline H-D-iGlu-D-Trp-OH which is D-isoglutamyl-D-tryptophan, as characterized by the XRPD pattern as illustrated in FIG. 1.

In another embodiment of the present invention, there is provided a method for preparing the mono ammonium salt of H-D-iGlu-D-Trp-OH, free from inorganic salts, which method comprises the following steps:

(a) preparing a solution of H-D-iGlu-D-Trp-OH acid addition salt in an aqueous medium essentially free of organic solvent;

(b) adjusting the pH to the predominant pH for monovalent salt form with a metal hydroxide solution;

(c) subjecting the solution from step (b) to an ion-exchange resin and elution with water to exchange the metal ion from the salt in the solution for hydrogen ion until the eluant is at a pH of about 5.7 to about 7.0;

(d) contacting the ion-exchange resin with an ammonia based regenerant solution operative to exchange ions therein for the H-D-iGlu-D-Trp-OH of interest contained in the ion-exchange resin, thereby to form a regenerant eluant containing the ammonium salt of H-D-iGlu-D-Trp-OH;

(e) solvent evaporation of the solution from step (d) to give the crude ammonium salt;

(f) dissolving the ammonium salt from step (e) in water and slowly adding isopropanol so that a precipitate of the mono ammonium salt is formed; and (g) vacuum drying the product from step (f) to give the crystalline form of H-D-iGlu-D-Trp-OH, ammonium salt (1:1).

Alternatively, in place of steps (f) and (g), the method comprises the following steps:

(h) subjecting the material from step (e) to silica gel chromatography with isopropanol and ammonia solution as the eluant; and (i) freeze-drying the product from step (h) to give the amorphous form of H-D-iGlu-D-Trp-OH, ammonium salt (1:1).

In another embodiment of the present invention, there is provided a process for the preparation of the mono ammonium salt of H-D-iGlu-D-Trp-OH from crystalline H-D-iGlu-D-Trp-OH, free from inorganic salts, which process comprises the following steps:

(a) adding H-D-iGlu-D-Trp-OH to less than one equivalent of ammonium hydroxide solution;

(b) adjustment of the pH to 6 to 7 with ammonium hydroxide;

(c) solvent evaporation to give an oil; addition of isopropanol with stirring to cause the precipitation of the mono ammonium salt;

(d) recovering the precipitated H-D-iGlu-D-Trp-OH ammonium salt thereof; and (e) vacuum drying the product resulting from step (c) to give H-D-iGlu-D-Trp-OH mono ammonium salt.

In another embodiment of the present invention, there is provided the crystalline H-D-iGlu-D-Trp-OH, ammonium salt (1:1) which is characterized by the XRPD pattern expressed in the description of drawings.

In another embodiment of the present invention, there is provided the crystalline H-D-iGlu-D-Trp-OH, ammonium salt (1:1) which is characterized by the XRPD pattern as illustrated in FIG. 2.

In another embodiment of the present invention, there is provided the amorphous H-D-iGlu-D-Trp-OH, ammonium salt (1:1) which is characterized by the FTIR (infrared) spectrum as illustrated in FIG. 5.

In another embodiment of the present invention, there is provided a process for the preparation of an acid addition salt of D-isoglutamyl-D-tryptophan, wherein the salt is H-D-iGlu-D-Trp-OH hydrochloride, which process comprises:

(i) the base hydrolysis of a compound of formula I:

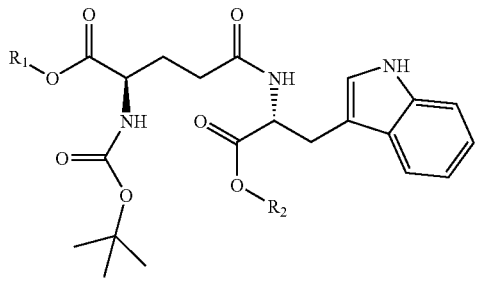

wherein $R^1$ is selected from the group consisting of $C_1$-$C_4$ alkyl and benzyl, and $R^2$ is $C_1$-$C_4$ alkyl with the proviso that $C_4$ alkyl is not tert-butyl, with metal hydroxide in water and an inert solvent in the presence of methanol to give Boc-D-iGlu-D-Trp-OH, free from other diastereomers;

(ii) hydrogen chloride deprotection of Boc-D-iGlu-D-Trp-OH from step (i) in an inert organic solvent; and solvent evaporation to give the hydrochloride salt of H-D-iGlu-D-Trp-OH.

In another embodiment of the present invention, there is provided a process for the preparation of a solution of the acid addition salt H-D-iGlu-D-Trp-OH hydrochloride, wherein the process comprises:

(a) the hydrogenation of a compound of formula II:

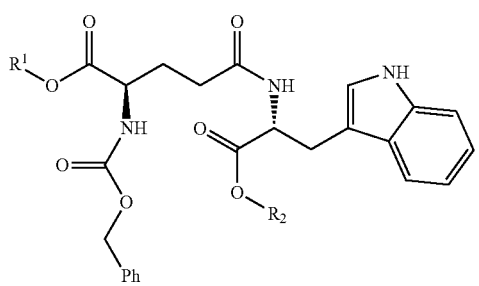

II wherein $R^1$ is benzyl and $R^2$ is selected from the group consisting of benzyl and hydrogen,
with palladium on charcoal in methanol or ethanol;

(b) purification of the crude H-D-iGlu-D-Trp-OH from step (a) with silica gel chromatography using isopropanol and water as an eluant; and (c) treatment of the material from step (b) with hydrochloric acid in water to give a solution of the H-D-iGlu-D-Trp-OH hydrochloride salt in water.

In the above two processes, the preparation of the acid addition salt of D-isoglutamyl-D-tryptophan from a compound of formula I is preferred over that from a compound of formula II because of the cost of chemical intermediates.

In another embodiment of the present invention, there is provided a process for the preparation of a solution of the base addition salt of H-D-iGlu-D-Trp-OH, wherein the process comprises:

(a) acid deprotection of the dipeptide N-Boc-D-Glu-(γ-D-Trp-OR²)-α-OR¹, wherein each of $R^1$ and $R^2$ is independently selected from the group consisting of $C_1$-$C_4$ alkyl and benzyl;

(b) base hydrolysis of the product from step (a) with a metal hydroxide in water and an inert solvent in the presence of methanol wherein the metal hydroxide is selected from the group consisting of sodium hydroxide, potassium hydroxide and lithium hydroxide;

(c) extraction of the material from step (b) with a water immiscible solvent and separating the aqueous layer;

(d) adjusting the pH of the aqueous phase from step (c) from about 6 to about 7; and (e) solvent evaporation of the solution from step (d) to produce a solution containing an estimated ratio of about a part solute to less than about 8 parts water wherein the solute is the base addition salt of D-isoglutamyl-D-tryptophan.

In another embodiment of the present invention, there is provided a novel diester derivative H-D-Glu-(γ-D-Trp-OR²)-α-OR¹ hydrochloride wherein each of $R^1$ and $R^2$ is independently selected from the group consisting of benzyl and $C_1$-$C_4$ alkyl.

The compounds H-D-Glu-(γ-D-Trp-OR²)-α-OR¹ are unknown in the prior art. These compounds can be used as intermediates for the preparation of the dipeptide D-isoglutamyl-D-tryptophan. Alternatively, H-D-Glu-(γ-D-Trp-OR²)-α-OR¹ hydrochloride may be used in a pharmaceutical preparation wherein the hydrolysis of the ester takes place in situ to give D-isoglutamyl-D-tryptophan when the formulation is prepared.

In an embodiment of the present invention, there is provided a speciation plot illustrated in FIG. 8 for the isolation of H-D-iGlu-D-Trp-OH at pH of about 2.5 to about 3.0.

Method of Preparation

The present invention provides, as depicted below in Scheme 5, a reliable methodology for the high yield synthesis of pure N-(tert-butoxycarbonyl)-D-isoglutamyl-D-tryptophan, which reliable methodology is absent in the prior art (for example, U.S. Pat. No. 5,736,519).

Scheme 5

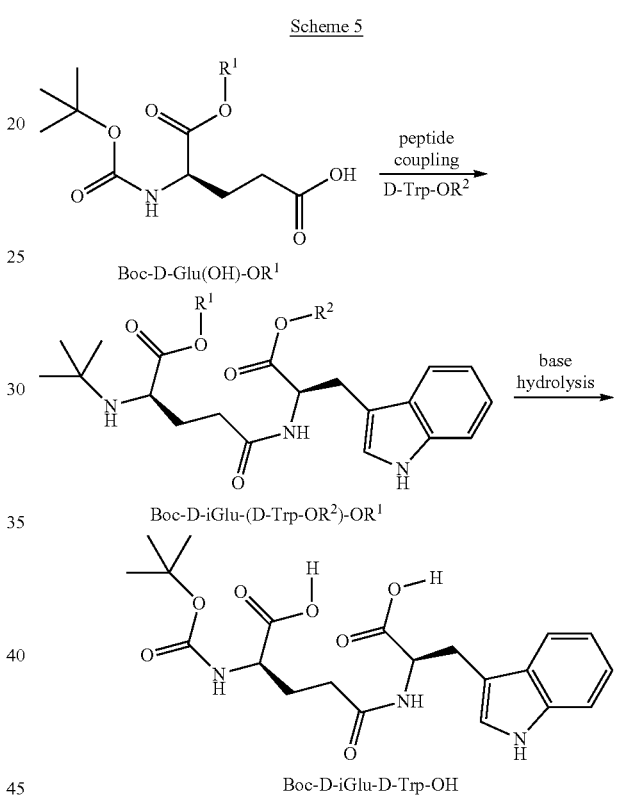

In the method of the present invention, a solution of Boc-D-Glu(OH)—OR¹ wherein $R^1$ is benzyl in an inert solvent is reacted with N-(3-dimethylaminopropyl)-N'-ethylcarbodiimide hydrochloride (EDC), hydroxybenzotriazole (HOBt) and diisopropylethylamine (DIPEA).

The preferred temperature is from about 5 to about −5° C. and the preferred solvent is dichloromethane. After mixing for about 5 to about 30 minutes, preferably about 15 minutes, a solution of the HCl salt of D-Trp-OR² wherein $R^2$ is methyl with diisopropylethylamine (DIPEA) is added dropwise. The resulting solution is stirred at the ice-cold temperature, preferably from about −5 to about 5° C. for about 1 hour and then at room temperature for about 12 to about 20 hrs, preferably about 16 hrs. The product Boc-D-iGlu-(D-Trp-OR²)-α-OR¹ is isolated by conventional means. The compound can be easily crystallized from ethyl acetate and hexanes. The two synthetic impurities present in trace amounts are compounds (A) and (B), which can be removed by recrystallization. Both compounds are believed to derive from the reagent HOBt.

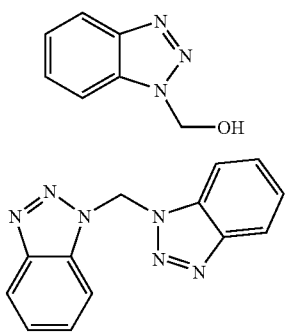

The diester Boc-D-Glu-(γ-D-Trp-OR$^2$)-α-OR$^1$ in alcohol is mixed with a solution of sodium hydroxide. The preferred amount of sodium hydroxide is about 2.5 to about 5 equivalents per equivalent of the diester. Still preferred, a molar ratio of about 2 to about 3.5 moles of NaOH per mole of the diester compound is used. The preferred ratio of solvent is about 2 mL of alcohol per mL of water, and the preferred ratio of NaOH to water is about 1 g to 20 mL. This isolation procedure involves the extraction of the reaction mixture with ethyl acetate, thus any organic impurity is removed at this stage of the synthesis. Upon acidification, the aqueous fraction is extracted with an organic solvent such as ethyl acetate. The diacid N-(tert-butoxycarbonyl)-D-isoglutamyl-D-tryptophan (Boc-D-iGlu-D-Trp-OH) is isolated by conventional means as a solid. The isolated yield for the combined two steps is 89% yield. This is superior to the procedure in the prior art (U.S. Pat. No. 5,736,519). The novel process of the present invention is further illustrated in the examples below.

Detailed investigation and monitoring of the hydrolysis step by the present applicant showed that the compound Boc-D-iGlu-(D-Trp-OR$^2$)—OR$^1$ wherein R$^1$ is benzyl and R$^2$ is methyl is first converted by the methanol to give Boc-D-iGlu-(D-Trp-OMe)-OMe, and then the compound is hydrolyzed into the diacid. The present applicant determined that the methanol is a requirement for the rapid hydrolysis of the alpha benzyl ester. In view of the large volume of ethyl acetate required for extraction of the product, the present applicant invented a two phase procedure for the efficient hydrolysis of Boc-D-iGlu-(D-Trp-OR$^2$)—OR$^1$. A mixture of Boc-D-iGlu-(D-Trp-OR$^2$)—OR$^1$ in tert-butyl methyl ether (MTBE) and a metal hydroxide solution such as lithium hydroxide or sodium hydroxide solution is stirred. The preferred ratio of metal hydroxide to Boc-D-iGlu-(D-Trp-OR$^2$)—OR$^1$ is between about 2.0-2.5 to 1. Methanol is added and the mixture is vigorously stirred for about 1 to about 6 hrs, preferably from about 1.5 to about 2.5 hours. The mixture is isolated from the organic phase by conventional means. This procedure eliminates the use of large amount of ethyl acetate for extraction and is illustrated in the examples below.

In the conventional method, the compound Boc-D-iGlu-D-Trp-OH is deprotected with organic acids to give the dipeptide H-D-iGlu-D-Trp-OH which requires extensive purification. There are numerous shortcomings to the prior art procedures (U.S. Pat. No. 5,736,519) which use formic acid at 40° C. to deprotect a mixture of Boc-D-iGlu-D-Trp-OH and Boc-D-Glu-D-Trp-OH to give a mixture of H-D-iGlu-D-Trp-OH and H-D-Glu-D-Trp-OH. Ion exchange chromatography and reverse HPLC are used to isolate the product. The recovery is low and the procedure is not amenable to large scale production. The deprotection of N-tert-butoxycarbonyl group with trifluoroacetic acid or formic acid generates tert-butyl carbonium ion which may react with the indole nitrogen to form the N-tert-butyl product (Löw, M., et. al. (1978), Hoppe-Seyler's Z. Physiol. Chem., 359(12):1643-51). The formation of the glutarimide (1.8) (Pandit, U.K. (1989), Pure & Appl. Chem., Vol. 61, No. 3, pp. 423-426) is another concern.

The present applicant determined that the acid addition salt of the present invention, in particular the crude hydrochloride salt, can be easily prepared with HCl in an inert solvent such as ethyl acetate at low temperature, preferably from about 0° C. to about ambient temperature. Solvent evaporation afforded the thymodepressin hydrochloride which is used towards the preparation of thymodepressin.

In predicting the required pH for the precipitation of thymodepressin in its diacid form H-D-iGlu-D-Trp-OH, the present applicant has conducted a theoretical calculation on a speciation plot and has concluded that thymodepressin exists in the diacid form at pH of about 2.5 to about 3.0. This conclusion led us to a method of isolation of thymodepressin without chromatography.

FIG. 7 illustrates such a calculation. In FIG. 7, LH$_2$ is the dicarboxylic acid form of the peptide H-D-iGlu-D-Trp-OH (i.e., thymodepressin), LH is the monocarboxylic acid salt form of the peptide H-D-iGlu-D-Trp-OH; one such example being the monoammonium salt, L is the dicarboxylic acid salt form of the peptide H-D-iGlu-D-Trp-OH; one such example being the disodium salt, and LH$_3$ is the acid addition salt of thymodepressin. The X axis provides the pH of the solution. The Y axis provides the % formation relative to L (the default terminology of the software) and reports the molar fraction of the species present at a particular pH. At a pH of about 2.5 to, about 3.0, the majority (80%) of the dipeptide exists as the dicarboxylic acid form and can be precipitated out of solution if it is insoluble in water. Our investigation shows that the dicarboxylic acid form prepared by this method has a water solubility of about 23 mg per mL. At a pH of about 7.0, 100% of the species is in the monocarboxylic acid form. If the counter ion is sodium, then the species is monosodium thymodepressin.

In practice, when a solution of the hydrochloride salt of thymodepressin is dissolved in water and the pH is adjusted to about 3.0 with stirring, a solid slowly appears and is filtered from the mixture. The LC purity of the material exceeds 97% and falls within the pharmaceutical grade purity as an active pharmaceutical ingredient. We determined that this method is superior to prior art in the manufacturing and isolation of pure thymodepressin (H-D-iGlu-D-Trp-OH). No ion exchange and reverse phase preparative column chromatography are required because the only by-product is sodium chloride, which is soluble in water. This is a direct procedure for the separation and purification of thymodepressin. It is predicted by theoretical speciation plot, and the process is superior to prior art procedures which require tedious purification.

The pKas of the acid and amine groups of H-D-iGlu-D-Trp-OH are experimentally determined. The speciation plot of the dipeptide using experimentally determined pKas is shown in FIG. 8. In FIG. 8, LH$_2$ is thymodepressin, LH is the monocarboxylic acid salt, L is the dicarboxylic acid salt, and LH$_3$ is the acid addition salt of thymodepressin. The X axis provides the pH of the solution. The Y axis provides the % formation relative to L (the default terminology of the software) and reports the molar fraction of the species present at a particular pH. The concentration of 0.5M is used to reflect the equivalency of 1 gm of thymodepressin in 6 ml water during isolation purposes. This figure shows that about 75% of the thymodepressin (LH$_2$) exists in the dicarboxylic acid form at pH 2.7. For this reason, thymodepressin precipitates at pH 2.7 and can be filtered. The mother liquor can be concentrated to obtain a second crop of thymodepressin. The plot confirms the theoretical prediction that the diacid form of H-D-iGlu-D-Trp-OH predominates at pH of about 2.5 to about 3.0, which is the pH for the isolation of the diacid from water as a precipitate. Since only about 80% of the material will precipitate in pure form, the mother liquor should be reduced in volume and subjected to a second round of precipitation at pH of about 2.5 to about 3.0, preferably at pH of about 2.7.

The deprotection of Boc-H-D-iGlu-D-Trp-OH with trifluoroacetic acid in an inert solvent affords the trifluoroacetic acid salt. The inert solvent is dichloromethane and usually a 1:1 mixture of trifluoroacetic acid and dichloromethane is used. Solvent evaporation affords an oil which is vacuum dried to remove residual solvent. The oil is dispersed in water. When the pH is adjusted to about 3.0, a white solid appears after stirring for about 12 to about 16 hrs.

In the preparation of the acid addition salt, it is preferable to use HCl in an inert solvent to produce the hydrochloride salt. Alternatively, the trifluoroacetic acid salt can be produced using the method above. The use of the hydrochloric acid salt as the acid addition salt is preferred because the deprotection of Boc-D-iGlu-D-Trp-OH is more efficient with HCl in an inert solvent such as 3M HCl in ethyl acetate. The reaction time is significantly longer with trifluoroacetic acid. In addition, the trifluoroacetic acid salt of D-iGlu-D-Trp-OH contains several synthetic impurities, which carry over to the D-iGlu-D-Trp-OH upon precipitation at pH of about 2.5 to about 3.0 in water. The impurities must be removed by extensive recrystallization.

The starting material Boc-D-iGlu-D-Trp-OH is prepared using the methodology as described earlier. The acid addition salt should be vacuum dried to ensure it is free from organic solvent and volatile impurities. In the precipitation of thymodepressin in water, a solution of the acid addition in water is prepared. The ratio of acid addition salt to water is in the range of about 1:5 to about 1:10. Still preferred, the ratio of acid addition salt is in the range of about 1:6 to about 1:8. A metal hydroxide solution, normally a sodium hydroxide solution is used to precipitate the product, but potassium hydroxide and other metal hydroxide solutions can be used.

Crude H-D-iGlu-D-Trp-OH can also be prepared by the hydrogenation of a compound of formula II:

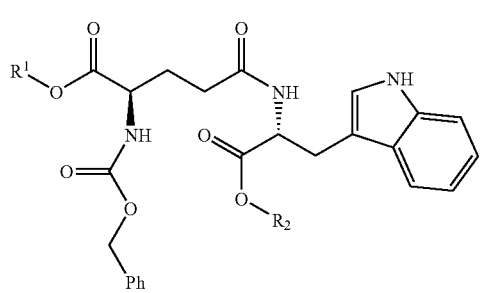

II wherein $R^1$ is benzyl and $R^2$ is selected from the group consisting of benzyl and hydrogen, with palladium on charcoal in methanol or ethanol. After filtration of the catalyst, the filtrate is evaporated to an oil, which is further purified with silica gel chromatography using isopropanol and water as an eluant. The H-D-iGlu-D-Trp-OH obtained can be converted to the H-D-iGlu-D-Trp-OH hydrochloride salt in water with hydrochloric acid.

A solution of the base addition salt of D-isoglutamyl-D-tryptophan is prepared by the acid deprotection of the dipeptide Boc-D-Glu-(γ-D-Trp-OR$^2$)-α-OR$^1$, wherein each of $R^1$ and $R^2$ is independently selected from the group consisting of benzyl and $C_1$-$C_4$ alkyl. For example, HCl deprotection of Boc-D-Glu-(γ-D-Trp-OR$^2$)-α-OR$^1$ in an inert solvent such as dichloromethane, affords the HCl salt of H-D-Glu-(γ-D-Trp-OR$^2$)-α-OR$^1$. For the combination where $R^1$ is benzyl and $R^2$ is methyl, the product HCl.H-D-Glu-(γ-D-Trp-OR$^2$)-α-OR$^1$ precipitates out of dichloromethane and can be removed by filtration. Treatment of the acid addition salt with a metal hydroxide in an inert solvent such as methanol for one phase homogeneous hydrolysis or with tert-butyl methyl ether for two phase hydrolysis affords H-D-iGlu-D-Trp-OH base addition salt in solution. Upon extraction of the reaction mixture with a water immiscible solvent such as ethyl acetate or tert-butyl methyl ether, the aqueous phase is neutralized to pH of about 6 to about 7 and the solution is evaporated to reduced the volume to an estimated ratio of less than about 1 part solute:8 parts water. The solute, as predicted by the speciation calculations as shown in FIG. 8, is the base addition salt (in mono carboxylate form) of H-D-iGlu-D-Trp-OH. If sodium hydroxide is used as the metal hydroxide, the solute will be the mono sodium form of the H-D-iGlu-D-Trp-OH in water. Adjustment of this solution to pH of about 2.5 to about 3.0 will result in the precipitation of solid thymodepressin, H-D-iGlu-D-Trp-OH.

The mono ammonium salt of thymodepressin can be prepared directly from the Boc-D-iGlu-D-Trp-OH dipeptide. The crude acid addition salt such as the hydrochloride salt, prepared in the manner as described above, is treated with ion exchange resin to remove the inorganic salt. Thus, a solution of the crude thymodepressin hydrochloride is dissolved in water and adjusted to pH of about 6 to about 8. The solution is treated with ion exchange resin. The preferred resin is a sulfonic acid based resin. An example of such is AMBERLYST® 15. The inorganic salt is removed by washing with water until pH of about 5.7 to about 7. Ammonia is used as a regenerant to recover the ammonium salt of thymodepressin from the resin. It is preferred to use concentrated ammonia and isopropanol as a regenerant. The preferred ratio is concentrated ammonia and isopropanol in the ratio of about 1 to about 3-4, with the final wash using concentrated ammonia and isopropanol in the ratio of 1 part concentrated ammonia:1 part water:2 part isopropanol. The ammonia wash is evaporated under reduced pressure to an oil, which is crystallized with isopropanol and water to give the mono ammonia salt as a white solid. The preferred ratio of isopropanol to water for recrystallization is in the range of about 5:1 to about 10:1. Column chromatography is not required.

There is no method for the purification of thymodepressin reported in the prior art other than reverse phase preparative liquid chromatography. This method is extremely time consuming and expensive, and is not amenable to large scale production. The present applicant has determined that crude thymodepressin can also be purified to pharmaceutical grade purity by flash silica gel chromatography with isopropanol and water as an eluant. The preferred mobile phase is isopropanol:water in the range of about 10:1 to about 5:1. The product is isolated by conventional means.

In a similar manner, the mono ammonium salt can also be purified by flash silica gel chromatography with isopropanol and concentrated ammonia as an eluant. The preferred mobile phase is isopropanol:ammonia in the range of about 10:1 to about 5:1. The product is isolated by conventional means.

The D-isoglutamyl-D-tryptophan mono ammonium salt obtained from crystallization using isopropanol and water is crystalline. On the other hand, when a solution of D-isoglutamyl-D-tryptophan mono ammonium salt is freeze-dried, the amorphous material is obtained.

Extensive study was conducted to confirm that there is no racemization of the chiral centers in the column purification and throughout the reaction sequence, and the details are shown in the examples below.

According to the present invention, a method is provided for the synthesis of Boc-D-iGlu-D-Trp-OH, free from the alpha amide isomer. A method is provided to convert the Boc-D-iGlu-D-Trp-OH to the acid addition salt of thymodepressin, in particular the hydrochloride salt. Speciation plot prediction affords a method for the precipitation of thymodepressin in pure form at a pH of about 3 in water. In addition, a method is provided to clean up less than 97% pure thymodepressin by flash column chromatography using isopropanol and water as an eluant. Another aspect of this invention involves a convenient method for the preparation of the mono ammonium salt from the hydrochloride salt of thymodepressin. The inorganic salt is removed by ion exchange resin and the mono ammonium salt recovered by using an ammonia based regenerant solution. The mono ammonium salt can be obtained by crystallization in pure form. A method is also provided to purify mono ammonium salt of lower purity by flash silica gel column chromatography using isopropanol and water as an eluant.

Further, the method for the synthesis of thymodepressin disclosed in the prior art (U.S. Pat. No. 5,736,519) generates crude thymodepressin which must be purified by ion exchange chromatography and reverse phase preparative liquid chromatography. The separation of the alpha amide product H-D-Glu-D-Trp-OH from gamma amide product thymodepressin D-1-D-Glu-D-Trp-OH remains a very serious production issue. The purification sequence listed in the prior art is unsuitable for large scale manufacturing.

Utility and Administration

The disodium salt of thymodepressin has been used for the treatment of psoriasis. Therefore the crystalline thymodepressin and thymodepressin mono ammonium salt of the present invention may be formulated into pharmaceutical compositions for administration to subjects in a therapeutically active amount and in a biologically compatible form suitable for in vivo administration, i.e., a form of the peptides to be administered in which any toxic effects are outweighed by the therapeutic effects.

According to the speciation plot as shown in FIG. 8, the predominant species at neutral pH is the mono carboxylate form of thymodepressin, that is, the mono sodium salt of the dipeptide D-isoglutamyl-D-tryptophan if the counterion is sodium. The disodium salt of D-isoglutamyl-D-tryptophan is extremely hygroscopic and is very difficult to handle for dispensing. The crystalline thymodepressin of the present invention has the XRPD characteristics as detailed in FIG. 1 and has a water solubility of about 20 mg per ml in water. It is an ideal candidate to replace the disodium salt in the preparation of different formulations. Although a solution of D-isoglutamyl-D-tryptophan has a pH of about 3 in solution, it can be adjusted with sodium hydroxide, sodium carbonate or sodium bicarbonate solution to a pH of about 7 to about 7.4. The mono ammonium salt of the present invention exists in both crystalline and amorphous forms. Both forms of the mono ammonium salt are extremely soluble in water. Therefore, it is also an excellent candidate for formulation.

Administration of the novel crystalline thymodepressin and/or its mono ammonium salt as described herein can be via any of the accepted modes of administration for systemically active therapeutic medicaments. These methods include oral, parenteral and otherwise systemic, aerosol or topical forms.

Depending on the intended mode of administration, the compositions used may be in the form of solid, semi-solid or liquid dosage forms, such as, for example, tablets, suppositories, pills, capsules, powders, liquids, aerosols, suspensions, or the like, preferably in unit dosage forms suitable for single administration of precise dosages. The compositions will include at least one conventional pharmaceutical carrier or excipient and crystalline thymodepressin or its pharmaceutically acceptable mono ammonium salt and, in addition, may include other medicinal agents, pharmaceutical agents, carriers, adjuvants, etc.

For solid compositions, conventional non-toxic solid carriers including, for example, pharmaceutical grades of mannitol, lactose, starch, magnesium stearate, sodium saccharin, talcum, cellulose, glucose, sucrose, magnesium carbonate, and the like may be used. The active compound as defined above may be formulated as suppositories using, for example, polyalkylene glycols, for example, propylene glycol, as the carrier. Liquid pharmaceutically administerable compositions can, for example, be prepared by dissolving, dispersing, etc., the active compound as defined above and optional pharmaceutical adjuvants in a carrier, such as, for example, water, saline, aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, etc. Actual methods of preparing such dosage forms are known, or will be apparent, to those skilled in this art; for example, see Remington: The Science and Practice of Pharmacy, David B. Troy (Ed.), Lipincott Williams & Wilkins, Philadelphia, Pa., 21$^{st}$ Edition, 2006. The composition or formulation to be administered will, in any event, contain a quantity of the active compound(s) in an amount effective to alleviate the symptoms of the subject being treated.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents and the like, such as for example, sodium acetate, sorbitan monolaurate, triethanolamine oleate, etc.

For thymodepressin or its mono ammonium salt, either oral or nasal (bronchial) administration is preferred, depending on the nature of the disorder being treated. For oral administration, a pharmaceutically acceptable non-toxic composition is formed by the incorporation of any of the normally employed excipients, such as, for example pharmaceutical grades of mannitol, lactose, starch, magnesium stearate, sodium saccharin, talcum, cellulose, glucose, sucrose, magnesium, carbonate, and the like. Such compositions take the form of solutions, suspensions, tablets, pills, capsules, powders, sustained release formulations and the like. Such compositions may contain from about 1% to about 95% active ingredient, preferably from about 25% to about 70%.

Oral and nasal administration to the lungs can also be effected by aerosol delivery forms. For aerosol administration, the active ingredient is preferably supplied in finely divided form along with a surfactant and a propellant. Typical percentages of active ingredients are from about 0.01 to about 20% by weight, preferably from about 0.04% to about 1.0%.

Surfactants must, of course, be non-toxic, and preferably soluble in the propellant. Representative of such agents are the esters or partial esters of fatty acids containing from 6 to 22 carbon atoms, such as caproic, octanoic, lauric, palmitic, stearic, linoleic, linolenic, olestearic and oleic acids with an aliphatic polyhydric alcohol or its cyclic anhydride such as, for example, ethylene glycol, glycerol, erythritol, arabitol, mannitol, sorbitol, the hexitol anhydrides derived from sorbitol (the sorbitan esters sold under the name SPAN®) and the polyoxyethylene and polyoxypropylene derivatives of these esters. Mixed esters, such as mixed or natural glycerides may be employed. The preferred surface-active agents are the oleates or sorbitan, e.g., those sold under the names ARLACEL®C (Sorbitan sesquioleate), SPAN®80 (sorbitan monooleate) and SPAN®85 (sorbitan trioleate). The surfactant may constitute from about 0.1% to about 20% by weight of the composition, preferably from about 0.25% to about 5%.

The balance of the composition is ordinarily propellant. Liquefied propellants are typically gases at ambient conditions, and are condensed under pressure. Among suitable liquefied propellants are the lower alkanes containing up to five carbons, such as butane and propane; and preferably fluorinated or fluorochlorinated alkanes, such as are sold under the name FREON®. Mixtures of the above may also be employed.

In producing the aerosol, a container equipped with a suitable valve is filled with the appropriate propellant, containing the finely divided active ingredient and surfactant. The ingredients are thus maintained at an elevated pressure until released by action of the valve.

For topical administration, these compositions comprise an effective amount of a compound of this class in admixture with at least one pharmaceutically acceptable non-toxic carrier. A suitable range of composition would be from about 0.1% to about 10% active ingredient, and the balance being the carriers, preferably from about 1% to about 2% active ingredient. The concentration of active ingredient in pharmaceutical compositions suitable for topical application will vary depending upon the particular activity of the compound used in conjunction with the condition and subject to be treated. Suitable carriers or medicament vehicles for topical application of these compounds include creams, ointments, lotions, emulsions, solutions and the like.

For example, a suitable ointment for topical application of the compounds of the present invention contains from about 15 to about 45 percent of a saturated fatty alcohol, having 16 to 24 carbon atoms such as cetyl alcohol, stearyl alcohol, behenyl alcohol, and the like, and from about 45 to about 85 wt. percent of a glycol solvent such as propylene glycol, polyethylene glycol, dipropylene glycol, and mixtures thereof. The ointment can also contain from about 0 to about 15 wt. percent of a plasticizer such as polyethylene glycol, 1,2,6-hexanetriol, sorbitol, glycerol, and the like; from about 0 to about 15 wt. percent of a coupling agent such as a saturated fatty acid having from 16 to 24 carbon atoms, e.g., stearic acid, palmitic acid, behenic acid, a fatty acid amide e.g., oleamide, palmitamide, stearamide, behenamide and an ester of a fatty acid having from 16 to 24 carbon atoms such as sorbitol monostearate, polyethylene glycol monostearate, polypropylene glycol or the corresponding mono-ester of other fatty acids such as oleic acid and palmitic acid; and from about 0 to about 20 wt. percent of a penetrant such as dimethyl sulfoxide or dimethylacetamide.

A therapeutically active amount of crystalline thymodepressin or its ammonium salt may vary according to factors such as disease state, age, sex, and weight of the individual. Dosage regime may be altered to provide the optimum therapeutic response. Generally, the daily regimen should be in the range of from about 1 to about 200 mg of peptide.

The following are examples of representative formulations and in no way restrict the scope of in the preparation of different pharmaceutical compositions:

| Ingredients | Quantity per tablet (mgs) |
| --- | --- |
| Active ingredient | 25 |
| lactose, spray-dried | 20 |
| corn starch | 153 |
| magnesium stearate | 2 |

The above ingredients are thoroughly mixed and pressed into single scored tablets.

| Ingredients | Quantity per tablet (mgs) |
| --- | --- |
| Active ingredient | 100 |
| lactose, spray-dried | 148 |
| magnesium stearate | 2 |

The above ingredients are mixed and introduced into a hard-shell gelatin capsule.

| Ingredients | Quantity per tablet (mgs) |
| --- | --- |
| Active ingredient | 200 |
| lactose | 145 |
| corn starch | 50 |
| magnesium stearate | 5 |

The above ingredients are mixed intimately and pressed into single scored tablets.

| Ingredients | Quantity per tablet (mgs) |
| --- | --- |
| Active ingredient | 108 |
| lactose | 15 |
| corn starch | 25 |
| magnesium stearate | 2 |

The above ingredients are mixed and introduced into a hard-shell gelatin capsule.

| Ingredients | Quantity per tablet (mgs) |
| --- | --- |
| Active ingredient | 150 |
| lactose | 92 |

The above ingredients are mixed and introduced into a hard-shell gelatin capsule.

An injectable preparation buffered to a pH of about 7 is prepared having the following composition:

| Ingredients | |
|---|---|
| Active ingredient | 0.2 g |
| KH$_2$PO$_4$ | 2 ml |
| KOH (1N) | q.s. to pH 7 |
| Water (distilled, sterile) | q.s. to 20 ml |

An injectable preparation buffered to a pH of about 7 is prepared having the following composition:

| Ingredients | |
|---|---|
| Active ingredient | 0.01 g |
| Water (distilled, sterile) | q.s. to 1 ml |
| NaOH (0.2N) | q.s. to pH 7 |

An oral suspension is prepared having the following composition:

| Ingredients | |
|---|---|
| Active ingredient | 0.1 g |
| fumaric acid | 0.5 g |
| methyl paraben | 2.0 g |
| granulated sugar | 0.1 g |
| sorbitol (70% solution) | 25.5 g |
| VEEGUM ® K (Vanderbilt Co.) | 12.85 g |
| Flavoring | 1.0 g |
| Colorings | 0.035 ml |
| distilled water | q.s. to 100 ml |

Topical Formulation

| Ingredients | Grams |
|---|---|
| Active compound | 0.2-2 |
| SPAN ® 60 | 2 |
| TWEEN ® 60 | 2 |
| Mineral oil | 5 |
| Petrolatum | 10 |
| Methyl paraben | 0.15 |
| Propyl paraben | 0.05 |
| BHA (butylated hydroxy anisole) | 0.01 |
| distilled water | q.s. 100 ml |

All of the above ingredients, except water, are combined and heated to about 45 degrees C. with stirring. A sufficient quantity of water at about 45 degrees C. is then added with vigorous stirring to emulsify the ingredients, and water then added q.s. 100 g.

In the following, the present invention is explained in detail referring to Examples, but the present invention is not limited thereto by any means.

EXAMPLE 1

Preparation of N-α-tert-butoxycarbonyl-γ-D-glutamyl(α-benzyl ester)-D-tryptophan methyl ester or (2R)-tert-Butoxycarbonylamino-(4R)-[2-(1H-indol-3-yl)-1-methoxycarbonyl-ethylcarbamoyl]-butyric acid benzyl ester or N-t-Boc-D-Glu-(γ-D-Trp-OMe)-α-OBzl}.

Procedure 1A:
Preparation of a Pure Reference Sample of N-t-Boc-D-Glu-(γ-D-Trp-OMe)-α-OBzl, using Silica Gel Chromatography Purification To a stirred ice-cooled solution of Boc-D-Glu-OBzl (6.00 g, 17.8 mmol) in CH$_2$Cl$_2$ (70 mL) was successively added EDC (5.11 g, 26.6 mmol), HOBt (3.60 g, 26.6 mmol) and DIPEA (4.60 mL, 26.6 mmol). Then, a solution of H-D-Trp-OMe.HCl (6.77 g, 26.6 mmol) and DIPEA (4.60 mL, 26.6 mmol) in CH$_2$Cl$_2$ (50 mL) was added dropwise. The resulting mixture was stirred at ice-cold temperature (−3° C. to 0° C.) for 1 h, then allowed to warm to room temperature, and stirred for 16 h. The reaction mixture was evaporated to dryness. The residue was partitioned between EtOAc and a saturated solution of NaHCO$_3$. The organic fraction was collected, washed with 10% citric acid, followed by brine. The organic layer was dried over Na$_2$SO$_4$, filtered and concentrated to a thick oil. The residue was purified by column chromatography on silica gel using a solvent gradient of a mixture of hexanes and EtOAc (8/2, 7/3 and 3/7 ratio, v/v) as eluant to afford the title product (9.40 g, 98%) as a white solid. $^1$H NMR (DMSO-d$_6$) δ ppm 10.86 (s, 1H), 8.31 (d, J=7.4 Hz, 1H), 7.49 (d, J=7.7 Hz, 1H), 7.31-7.35 (m, 7H), 7.14 (d, J=2.0 Hz, 1H), 7.06 (t, J=7.9 Hz, 1H), 6.98 (t, J=6.8 Hz, 1H), 5.12 (q, J=5.9 Hz, 2H), 4.5 (q, J=6.5 Hz, 1H), 3.96-4.03 (m, 1H), 3.55 (s, 3H), 2.98-3.16 (m, 2H), 2.18-2.24 (m, 2H), 1.86-1.95 (m, 1H), 1.71-1.80 (m, 1H), 1.37 (s, 9H); $^{13}$C NMR (DMSO-d$_6$) δ ppm: 172.4 (C), 172.3 (C), 171.4 (C), 155.6 (C), 136.1 (C), 136.0 (C), 128.4 (CH), 127.9 (CH), 127.7 (CH), 127.1 (C), 123.6 (CH), 120.9 (CH), 118.4 (CH), 117.9 (CH), 111.4 (CH), 109.5 (C), 78.2 (C), 65.8 (CH$_2$), 53.3 (CH), 53.16 (CH), 51.7 (CH$_3$), 31.3 (CH$_2$), 28.2 (CH$_3$), 27.1 (CH$_2$), 26.4 (CH$_2$); MS (m/z) 538 [M+1]$^+$; Anal. Calcd. for C$_{29}$H$_{35}$N$_3$O$_7$.0.5H$_2$O: C, 63.72; H, 6.64; N, 7.69. Found: C, 63.79; H, 6.06; N, 7.65.

Procedure 1B:
Preparation of a Pure Sample of N-t-Boc-D-Glu-(γ-D-Trp-OMe)-α-OBzl by Recrystallization A suspension of Boc-D-Glu-OBzl (60.26 g, 178.6 mmol) in CH$_2$Cl$_2$ (335 mL) was cooled to ca. −1° C., and stirred for 15 min. Then, DIPEA (46.70 mL, 268.0 mmol), HOBt (36.20 g, 268.0 mmol), EDC (51.38 g, 268.0 mmol) were successively added. Afterwards, a solution of H-D-Trp-OMe.HCl (68.25 g, 268.0 mmol) and DIPEA (46.70 mL, 268.0 mmol) in CH$_2$Cl$_2$ (187 mL) was added dropwise. The resulting mixture was stirred at ice-cold temperature (−1° C. to −5° C.) for 2 h, then allowed to warm to room temperature, and stirred for overnight under a blanket of nitrogen.

The reaction mixture was evaporated to dryness. The residue was partitioned between EtOAc (200 mL), a saturated solution of Na$_2$CO$_3$ (100 mL) and H$_2$O (150 mL). The aqueous layer was extracted again with EtOAc (200 mL). The organic fractions were collected, washed with H$_2$O (100 mL), 10% citric acid (2×200 mL), and brine (60 mL). The organic layer was dried over Na$_2$SO$_4$, filtered and evaporated to dryness. The residue was dissolved in EtOAc (141 mL), then hexanes (106 mL) were added. The resultant suspension was stirred for 6 h, and filtered. The solid was thoroughly washed with hexanes (100 mL), then dried under vacuum in an oven at 40° C. for overnight. An off white solid was obtained (81.67 g, 85%). ¹H NMR data conforms to structure (see Example 1, Procedure 1A).

Procedure 1C:
Preparation of a Pure Sample of N-t-Boc-D-Glu-(γ-D-Trp-OMe)-α-OBzl without Chromatographic Purification and Determination of Synthetic Impurities Boc-D-Glu-OBzl (48.0 g, 142.2 mmol) was dissolved in 270 mL of dichloromethane and then cooled to 0-5° C. using an ice bath. HOBt (23.8 g, 156.4 mmol) was added followed by DIPEA (27.0 mL, 156.4 mmol) and stirred for 10 min. EDC (38 g, 199.1 mmol) and a premixed H-D-Trp-OMe solution (prepared from H-D-Trp-OMe.HCl (39.7 g, 156.4 mmol) and DIPEA (27.0 mL, 156.4 mmol) in 150 mL of dichloromethane stirred at room temperature for 20 min) were added successively to the solution. The reaction was stirred at 0° C. for 2 hours and then overnight at room temperature. The reaction was poured over 250 mL of distilled water and extracted. The organic layer was washed with 250 mL each of 10% citric acid, 2× with 5% NaHCO₃ solution and brine. The organic layer was dried over sodium sulfate and concentrated in vacuo to yield a pale yellow foamy solid.

The solid was dissolved in approximately 250 mL of ethyl acetate and evaporated to dryness. The operation was performed twice to form a waxy solid. To the solid material was added 100 mL of ethyl acetate and allowed to stir at room temperature. The mixture was stirred at a moderate to fast speed until a slurry-like suspension had formed—this process takes approximately 45 min (stirring for a prolonged period of time can result in solidification of the solution into a gelatin-like substance). Then, 75 mL of hexanes was added and the mixture was stirred for an additional 10 min. At this point, another 20 mL of ethyl acetate was added and the slurry was filtered immediately to give a fluffy pale pink solid. The solid was washed immediately three times with 30 mL of hexanes, which helped to remove the pinkish color. The filtrate was collected and was allowed to sit undisturbed for 40 minutes. A granular solid had precipitated out from the filtrate. The mixture was filtered and the solid was washed three times with 10 mL of hexanes.

The filtrate was collected and concentrated to a solid. The solid was dissolved in 20 mL of ethyl acetate and stirred until a slurry had formed. Then, 40 mL of hexanes was added and the mixture stirred for 5 min. The mixture was filtered and the collected solid was washed with hexanes. The combined solids were dried overnight in an oven (35° C.) under vacuum to constant weight. Thus, 59.0 g (77.2%) of the title compound was obtained. Mp: 83.1-87.5° C.; ¹H NMR data were identical to those described in Example 1, Procedure 1A; HPLC purity (PEAK AREA PERCENT): 97.2%; Retention time: 7.56 min; HPLC Conditions: Column Waters Symmetry C 18, 3.9×150 mm, 5 µm; Mobile phase: 0.035% HClO₄, pH 2/CH₃CN, gradient (min-% CH₃CN) 0-35, 10-90, 12-90; Flow rate: 1 mL/min; λ: 230, 260, 280 nm Analysis of Impurities in the Mother Liquor.

The result of the analysis of the mother liquor by TLC (50/50 EtOAc/Hexanes) is shown in the table below. Spots A and B are both UV active, but gave negative ninhydrin tests.

The product and baseline spots both gave positive ninhydrin tests. Samples of A and B have been isolated by column chromatography on silica gel, and their structures have been elucidated by ¹H NMR and MS/MS. The structures of A and B are shown below.

Rf Values in 50/50 EtOAc/Hexanes:

| Spot | Rf value |
|---|---|
| A | 0.80 |
| B | 0.60 |
| Product | 0.39 |

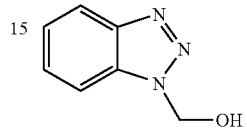

Spot A

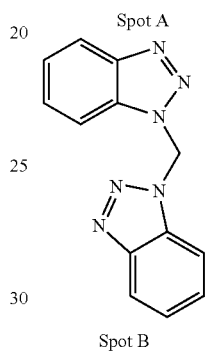

Spot B

Both spots A and B are impurities associated with HOBt. The impurities can be removed by recrystallization. Any trace impurities can be removed in the subsequent hydrolysis step.

EXAMPLE 2

Preparation of N-α-tert-butoxylcarbonyl-D-iso-glutamyl-D-tryptophan or (2R)-tert-butoxycarbonylamino-(4R)-[1-carboxy-2-(1H-indol-3-yl)-ethylcarbamoyl]-butyric acid or N-t-α-Boc-D-iGlu-D-Trp-OH Procedure 2A:
One Phase Hydrolysis with NaOH.

To a stirred solution of N-t-Boc-D-Glu-(γ-D-Trp-OMe)-α-OBzl (3.7 g, 6.9 mmol) from Example 1, Procedure 1A in MeOH (40 mL), was added a solution of NaOH (1.0 g, 25 mmol) in H₂O (20 mL). The resulting solution was stirred at room temperature overnight. The reaction mixture was poured into a 1 N solution of NaOH (100 mL), and the aqueous mixture was washed with EtOAc (2×100 mL). The aqueous layer was acidified with a 3N HCl solution, then extracted with EtOAc (2×50 mL). The organic fractions were combined, dried over Na₂SO₄ and evaporated to dryness under reduced pressure. A white solid was obtained (2.7 g, 91%). M.p. 148-158° C.; ¹H NMR (DMSO-d₆) δ ppm: 12.47 (br, 2H), 10.82 (s, 1H), 8.21 (d, J=7.8 Hz, 1H), 7.53 (d, J=7.8 Hz, 1H), 7.34 (d, J=8.1 Hz, 1H), 7.13 (d, J=2.0 Hz, 1H), 7.06 (t, J=7.5 Hz, 2H), 6.98 (t, J=7.4 Hz, 1H), 4.46 (q, J=5.3 Hz, 1H), 3.88-3.83 (m, 1H), 3.17-2.97 (dd, J=5.2 and 8.4 Hz, 2H), 2.23-2.10 (m, 2H), 1.90-1.82 (m, 1H), 1.75-1.68 (m, 1H), 1.38 (s, 9H); ¹³C NMR (DMSO-d₆) δ ppm: 173.9 (C), 173.4 (C), 171.5 (C), 155.6 (C), 136.1 (C), 127.2 (C), 123.5 (CH), 120.9 (CH), 118.4 (CH), 118.2 (CH), 111.4 (CH), 109.9 (C), 78.0 (C), 53.1 (CH), 52.9 (CH), 31.7 (CH$_2$), 28.2 (CH$_3$), 27.2 (CH$_2$), 26.7 (CH$_2$); FT-IR (KBr) v: 3415, 3338, 2986, 1719, 1686, 1654, 1534, 1424, 1366, 1252, 1169, 1069, 744, 634, 429 cm$^{-1}$; MS (m/z) 434 [M+1]$^+$.

Procedure 2B:
One Phase Hydrolysis with LiOH.

To a stirred ice-cooled (0° C. to 5° C.) solution of Boc-D-Glu-(γ-D-Trp-OCH$_3$)-α-OBzl (46.06 g, 85.68 mmol) in MeOH (200 mL) was added a solution of LiOH (10.78 g, 257.0 mmol) in H$_2$O (136 mL). The resulting solution was stirred and maintained between 0° C. to 10° C. for 3 h. The reaction mixture was poured into a saturated solution of Na$_2$CO$_3$ (100 mL) and H$_2$O (150 mL), the aqueous mixture was washed with EtOAc (2×150 mL). The aqueous layer was acidified to pH=2-3 with a 3N HCl solution, then extracted with EtOAc (2×200 mL). The organic fractions were combined, dried over Na$_2$SO$_4$ and evaporated to dryness under reduced pressure. A white solid was obtained (36.65 g, 98.7%). $^1$H NMR and MS/MS data conform to structure (see Example 2, Procedure 2A).

Procedure 2C:
Preparation of Boc-D-iGlu-D-Trp-OH without Chromatographic Purification Using a Two Phase Hydrolysis Process Lithium hydroxide (4.1 g, 97.7 mmol) was dissolved in 35 mL of distilled water. Then, 65 mL of methyl t-butyl ether (MTBE) was added followed by the dipeptide, Boc-D-Glu-(γ-D-Trp-OCH$_3$)-α-OBzl, (25 g, 46.5 mmol) obtained as described in Example 1. A very thick suspension formed immediately and 15 mL of methanol and 15 of MTBE were added under vigorous stirring. An additional 2 mL of methanol was added and the solids slowly dissolved over approximately 5 min. Once all material had dissolved, the solution was a yellow/green color with the top organic phase having a pale green color and the aqueous phase a yellow color. The reaction was allowed to stir vigorously at room temperature for 80 min, at which time, no starting material remained in the organic phase and the aqueous phase contained the product (TLC monitoring: 1/1 EtOAC/Hexanes, v/v). The solution was poured into a separatory funnel and the 2 phases separated. The organic phase was washed with 15 mL of water. The organic phase turned pink upon washing with water. The combined aqueous phase was washed twice with 30 mL of ethyl acetate. The aqueous phase was acidified to ca. pH 2 by adding dropwise 16.6 mL of 6N hydrochloric acid at room temperature. The aqueous phase was extracted twice with 50 mL of ethyl acetate. A minimum amount of methanol was added during the second extraction to help with solubility of the product in the organic layer. The combined organics were dried over sodium sulfate and concentrated in vacuo from a yellow liquid to yield a white solid. The solid was dried overnight in an oven (28° C.) under vacuum to constant weight.

Thus, 18.6 g (92% yield) of the title compound was obtained. Mp: 179.0-184.6° C.; $^1$H NMR data were identical to those described in Example 2A; HPLC purity (peak area percent): 98.3%; Retention time: 5.33 min; HPLC Conditions: Column Waters Symmetry C 18, 3.9×150 mm, 5 μm; Mobile phase: 0.035% HClO$_4$, pH 2/CH$_3$CN, gradient (T in min-% CH$_3$CN) 0-20, 10-90, 12-90; Flow rate: 1 mL/min; λ: 230, 260, 280 nm.

The above reaction can be monitored by HPLC. In Procedure 2C above, the presence of benzyl alcohol, arising from the hydrolysis of the benzyl ester moiety, can be observed on TLC (1/1 EtOAC/Hexanes, v/v, as eluant). Benzyl alcohol derives from the hydrolysis of the benzyl ester moiety. The first spot impurity is the same as in Example 1, Procedure 1C. Monitoring by HPLC and analysis by LC/MS indicated that Boc-D-Glu-(γ-D-Trp-OCH$_3$)-α-OBzl first reacted with the base and methanol to give Boc-D-Glu-(γ-D-Trp-OCH$_3$)-α-OCH$_3$, which then quickly hydrolyzed to give the diacid, Boc-D-Glu-(γ-D-Trp-OH)—OH or Boc-D-iGlu-D-Trp-OH.

EXAMPLE 3

Preparation of D-isoglutamyl-D-tryptophan

Procedure 3A:
Preparation of D-isoglutamyl-D-tryptophan and its Purification by Recrystallization Boc-D-iGlu-D-Trp-OH (20.0 g, 46.14 mmol, from Example 2) was placed in a 1 L-3-necked round bottom flask equipped with a mechanical stirrer. Ethyl acetate (300 mL) was added, and the resulting suspension was cooled to −10° C. in an ice-salt bath. HCl gas was bubbled into the cold suspension. A temperature range of −4° C. to −10° C. was maintained during the course of the reaction, and the progress of the reaction was monitored by HPLC. At a certain point the heterogeneous reaction mixture changed to a clear light pink homogenous solution. And after the starting material was consumed, the reaction mixture became to a suspension again. Volatile materials were then removed in vacuo to give a light pink solid. The solid was dissolved in 60 mL of deionized water, and the resulting solution was washed with dichloromethane (2×25 mL). The pH of the aqueous solution was then brought to ca. 3.0 by adding NaOH (10M, ca. 3.6 mL) under cooling. The resulting solution was filtered to remove any residual solid particulates. The filtrate was collected and stirred vigorously as a solid separated. The solid was collected by filtration. The filtrate was set aside for later use. The solid was then placed back in a round bottom flask, and 30 mL of deionized water was added. The mixture was stirred vigorously, and the solid was collected by filtration. The filtrate was set aside for later use. The solid was then washed with ice-cold deionized water (4×15 mL). The third aqueous wash solution was chloride free, as confirmed by a negative AgNO$_3$ test (a 4% solution was used). The solid was air dried, then placed in a vacuum oven at 36° C. overnight to give 8.5 g (HPLC purity (peak area percent): 98.3%).

Filtrates from the above steps were combined, and the same recrystallization procedure was carried out to give an additional 3.2 g of the product (HPLC purity (peak area percent): 98.7%). The combined yield of the 2 crops is 11.7 g (75%).

Further treatment of the final filtrate afforded a third crop (1.0 g, HPLC purity (peak area percent): 82.0%).

$^1$H NMR (D$_2$O—NaOD, pH 7.0) δ ppm: 7.64 (d, J=7.9 Hz, 1H), 7.43 (d, J=8.1 Hz, 1H), 7.19-7.16 (m, 2H), 7.10 (t, J=7.4 Hz, 1H), 4.52-4.48 (m, 1H), 3.48 (t, J=6.1 Hz, 1H), 3.34-3.29 (m, 1H), 3.08-3.02 (m, 1H), 2.30-2.17 (m, 2H), 1.92-1.75 (m, 2H). The XRPD spectrum of this material is shown in FIG. 1. HPLC method: Column: XTerra MS C18; 5 μm, 4.6×250 mm; Mobile phase: A=the aqueous phase: 4 mM Tris, 2 mM EDTA, pH 7.4; B=the organic phase: CH$_3$CN; the gradient program: B %: 0 min. 5%, 15 min. 55%, 30 min. 55%, 32 min. 5%, 40 min. 5%. Flow rate=1 mL/min; Injection volume= 5 μL; λ: 222, 254, 282, 450 nm; Retention time of the product=6.4 min.

Procedure 3B:
Ethyl acetate (250 mL), pre-cooled to 0° C., was saturated with HCl gas for 25 min. Boc-D-iGlu-D-Trp-OH (15.0 g, 34.6 mmol) was added, and a suspension formed. The solution was stirred for 90 min at ice bath temperature. The solvent was evaporated in vacuo to form a white solid. The solid was dissolved in 35 mL of distilled water, forming a thick light brown solution. The aqueous layer was washed twice with 30 mL of dichloromethane, then transferred to a 100 mL beaker. Using a pH electrode to monitor acidity, the pH was adjusted from 1.28 to 2.96 using 3.2 mL of 10N NaOH. The solution was stirred for 1 h at room temperature and a white precipitate slowly formed. The solid was collected by suction filtration, and thoroughly washed with water. The crude solid was suspended in 20 mL of distilled water and left stirring for 2 h at room temperature. The mixture was filtered, the solid was collected and dried to constant weight in an oven under vacuum overnight (40° C.). Thus, 8.6 g (74.5% yield) of the title compound was obtained. HPLC purity (peak area percent): 98.8% Retention time: 4.21 min; HPLC Conditions: Column Waters Symmetry C 18, 3.9×150 mm, 5 µm; Mobile phase: 0.035% $HClO_4$, pH 2/$CH_3CN$, gradient (T in min-% $CH_3CN$) 0-10, 10-90, 12-90; Flow rate: 1 mL/min; λ: 230, 260, 280 nm; $^1H$ NMR data conforms to structure.

EXAMPLE 4

Synthesis of D-isoglutamyl-D-tryptophan Mono Ammonium Salt (1:1) and its Isolation by Column Chromatography Purification Procedure 4A:

HCl gas was bubbled into a stirred ice-cooled (0° C. to 5° C.) solution of Boc-D-Glu-(-D-Trp-OH (2.5 g, 5.8 mmol) in EtOAc (60 mL) for 2.5 h. The reaction mixture was then evaporated to dryness. Purification of the residue by column chromatography on silica gel using a solvent gradient of a mixture of isopropanol and ammonium hydroxide (28-30% $NH_4OH$) (8/2 and 7/3 ratio, v/v) as eluant afforded the title product (1.8 g, 84.7%) as a white solid after solvent evaporation. M.p. 124-128° C.; $^1H$ NMR (DMSO-$d_6$) δ ppm: 10.98 (s, 1H), 8.25 (d, J=5.9 Hz, 1H), 7.53 (7.8 Hz, 1H), 7.30 (d, J=8.0 Hz, 1H), 7.17 (s, 1H), 7.00 (t, J=7.7 Hz, 1H), 6.92 (t, J=7.2 Hz, 1H), 4.28 (m, 1H), 3.22-3.31 (m, 2H), 2.90-2.96 (m, 1H), 2.23-2.25 (m, 2H), 1.97-1.98 (m, 1H), 1.84-1.86 (m, 1H); $^{13}C$ NMR (DMSO-$d_6$) δ ppm: 175.5 (C), 171.6 (C), 171.4 (C), 136.0 (C), 127.6 (C), 123.5 (CH), 120.5 (CH), 118.3 (CH), 117.9 (CH), 111.5 (C), 111.3 (CH), 55.3 (CH), 53.7 (CH), 32.5 ($CH_2$), 27.8 ($CH_2$), 27.4 ($CH_2$); $^{14}N$ NMR ($D_2O$) δ ppm: 20.4 (s); FT-IR (KBr) ν: 3406, 3055, 1581, 1456, 1399, 1341, 1096, 1009, 744, 535, 426 $cm^{-1}$; MS (m/z) 334 [Diacid+1]$^+$; Anal. Calcd. for $C_{16}H_{22}N_4O_5 \cdot H_2O$: C, 52.17; H, 6.57; N, 15.21. Found: C, 51.95; H, 6.84; N, 14.85. The substance is the mono ammonium salt of D-isoglutamyl-D-tryptophan (1:1). This material is amorphous as confirmed by XRPD.

Procedure 4B:

HCl gas is condensed into cold ethyl acetate (133.4 g) at −2° C. (external ice bath temperature) for 16 minutes. The weight increase of the solution is 21 g. Boc-D-iGlu-D-Trp-OH (3.8 g, 8.73 mmol) was dissolved in 50 mL of the above solution. The resulting mixture was maintained between 0 and 5° C. for 55 minutes. The reaction was monitored by TLC, then evaporated under reduced pressure (rotary evaporator temperature: 51-52° C.) to dryness. Purification by flash chromatography on silica gel using a solvent gradient of a mixture of isopropanol and ammonium hydroxide (28-30%) (8/2 and 7/3 ratio, v/v) as eluant afforded the product (2.0 g, 62%) as an off-white solid. The $^1H$ NMR data are similar to those reported in Example 4, Procedure 4A. This material is amorphous as confirmed by XRPD.

EXAMPLE 5

Synthesis of D-isoglutamyl-D-tryptophan, Mono Ammonium Salt (1:1)

Procedure 5A:

Synthesis of D-isoglutamyl-D-tryptophan, Mono Ammonium Salt (1:1) by Removal of Inorganic Salts using AMBERLYST®15 Resin Followed by Column Chromatographic Purification HCl gas was bubbled into a stirred ice-cooled (0° C. to 5° C.) suspension of Boc-D-iGlu-D-Trp-OH obtained (10.82 g, 24.96 mmol) in EtOAc (200 mL) for 2 h. The reaction mixture was then evaporated to dryness. The residue was dissolved in $H_2O$ (30 mL), and neutralized to pH=6-7 with 6N NaOH. The resulting solution was loaded onto a chromatography column packed with the AMBERLYST®15 resin, followed by elution of $H_2O$ until pH=5-5.5, then 100% isopropanol (pH=7) and finally 25% $NH_4OH$/IPA (pH=10).

Fractions containing the product were combined and evaporated to dryness under reduced pressure. Further purification of the residue by column chromatography on silica gel using a solvent gradient of a mixture of isopropanol and conc. ammonium hydroxide (17/3, 4/1 and 7/5 ratio, v/v) as eluant afforded the title product (6.68 g, 72.7%) as a light yellow foamy solid. $^1H$ NMR and MS/MS data conform to structure (see Procedure 4A). The water content as determined by the Karl-Fisher test was 3.7%.

Procedure 5B:

Synthesis of D-isoglutamyl-D-tryptophan, Mono Ammonium Salt (1:1) by Removal of Inorganic Salts using Amberlyst15 Resin Followed by Purification by Recrystallization To a stirred ice-cooled (0° C. to 5° C.) suspension of Boc-D-iGlu-D-Trp-OH (10.75 g, 24.80 mmol) in EtOAc (200 mL) was bubbled HCl gas. The reaction mixture was maintained in the ice bath (0° C. to 5° C.) for 2 h. TLC analysis (30% ammonia in isopropanol) showed the complete conversion of the starting material. The reaction mixture was evaporated to dryness in vacuo, the residue was dissolved in $H_2O$ (30 mL), and neutralized to pH=6-7 with 10N NaOH. The resulting homogenous solution was loaded onto a chromatography column packed with AMBERLYST®15 resin, followed by elution of $H_2O$ (2450 mL) until pH=4-5.5, isopropanol (1000 mL) and 25% $NH_4OH$/isopropanol. The fractions containing the product were combined and concentrated to dryness. A colorless foamy solid was obtained, to which was added isopropanol (150 mL) and $H_2O$ (30 mL). The resulting suspension was stirred at room temperature overnight. The solid was collected by suction filtration, thoroughly washed with isopropanol (2×60 mL), then EtOAc (2×60 mL), and finally dried under vacuum in an oven at 42° C. for overnight. An off white solid was obtained (6.60 g, 72.2%). $^1H$ NMR and MS/MS data conform to structure (see example 5). XRPD of this crystalline material is shown in FIG. 2. The water content as determined by the Karl-Fisher test was 5.9%.

EXAMPLE 6

Synthesis of D-isoglutamyl-D-tryptophan, Mono Ammonium Salt (1:1) from H-D-iGlu-D-Trp-OH Procedure 6A:
Preparation of D-isoglutamyl-D-tryptophan, Mono Ammonium Salt (1:1) Using CBz-D-Glu-(γ-D-Trp-OH)-γ-OBzl as an Intermediate EDC (562 mg, 2.93 mmol) was added to a solution of Z-D-Glu-OBz (990 mg, 2.67 mmol) and N-hydroxysuccinimide (337 mg, 2.93 mmol) in DMF (50 mL) at ice-water bath, and the resulting clear solution was stirred for overnight at RT. H-D-Trp-OH (640 mg, 3.13 mmol) and Et$_3$N (1 mL) was added at RT. After 20 minutes, the material was mixed with water and extracted with ethyl acetate. The combined EtOAc was washed with 10% citric acid and followed by brine, dried over Na$_2$SO$_4$, filtered, evaporated to dryness, dried under vacuum to give 1.49 g of the CBz-D-iGlu-(γ-OBzl)-D-Trp-OH. This material was hydrogenated with 33% (w/w) of 10% Pd/C at atmospheric pressure. After four hours, the catalyst was filtered through CELITE® and the filtrate was evaporated to give an oil. The crude product was purified by flash column chromatography using isopropanol/NH$_4$OH (80/20 to 70/30, v/v) as eluant to give the title compound (813 mg). MS/MS and $^1$H NMR data are similar to the compound obtained using the method shown in Example 4 above.

Procedure 6B:
Preparation of D-isoglutamyl-D-tryptophan, Mono Ammonium Salt (1:1) from H-D-iGlu-D-Trp-OH (see Example 3).

H-D-iGlu-D-Trp-OH (1 g from Example 3) was mixed with ammonium hydroxide (0.55M, 6 mL). The mixture was stirred and the pH was measured to be around 4.5. Ammonium hydroxide (0.55M) was added dropwise until the pH of the solution reached between 7.0 to 7.5. Volatile materials were removed in vacuo, and the residual oil was mixed with isopropanol. A white precipitate appeared. After 2 h, the solid ammonium salt was collected by suction filtration. The solid was dried to constant weight (1 g) under high vacuum for 12 h to give the D-isoglutamyl-D-tryptophan, ammonium salt (1:1). The water content as determined by the Karl-Fisher test was 4.6%.

EXAMPLE 7

Purification of H-D-iGlu-D-Trp-OH by Column Chromatography on Silica Gel using a Mixture of Isopropanol and Water A. Preparation of Cbz-D-Glu-(γ-D-Trp-OBzl)-α-OBzl To an ice-cooled solution of 2.67 g of Cbz-D-Glu-OBzl in 50 mL of DMF was added 0.91 g of N-hydroxysuccinimide (1.1 equiv.) and 1.52 g of EDC (1.1 equiv.), and the resulting solution was stirred at ice-water bath for 1 h and then at RT for overnight. To this reaction mixture was added 2.50 g of H-D-Trp-OBzl.HCl (1.05 equiv.) and 3 mL of Et$_3$N at RT. The reaction was complete after 1 h as monitored by HPLC.

The reaction mixture was quenched with deionized-water at ice-water bath, and then extracted with EtOAc several times. The combined EtOAc extracts was washed with 10% citric acid, followed by brine, dried over Na$_2$SO$_4$, filtered, and evaporated to dryness. The residue was coated onto silica gel in MeOH and the mixture was concentrated in vacuo. The latter was applied on top of a wet-packed silica gel column and the desired product, Cbz-D-Glu-(γ-D-Trp-OBzl)-α-OBzl, was eluted using a solvent gradient mixture (EtOAc/Hexanes, from 80/20 to 100/0). The desired fractions were combined and concentrated in vacuo to afford 4.64 g (99.6% yield) of title compound. HPLC purity (peak area percent): 93%; HPLC conditions: Column: Symmetry C18, 3.9×150 mm, 5 μm; Mobile phase: 0.035% HClO$_4$ (pH=2.5)/CH$_3$CN=gradient (min-CH$_3$CN %: 0-10, 10-100, 12-100, 14-50); Flow rate: 1 mL/min; λ: 280 nm; Retention time: 9.7 min.

B. Purification of D-Isoglutamyl-D-Tryptophan by Column Chromatography using a Mixture of Isopropanol and Water To a suspension of 4.0 g of Cbz-D-Glu-(γ-D-Trp-OBzl)-α-OBzl prepared as described in Example 7A above in 150 mL of 95/5 MeOH/H$_2$O (v/v) was added 1.5 g of Pd/C (37.5% w/w). The mixture was hydrogenated under 30 psi hydrogen pressure. The reaction was done after 75 min as monitored by HPLC. The catalyst was filtered off over a bed of CELITE® and the filtrate was concentrated under reduced pressure at 45° C. The residue was then purified by flash chromatography on silica gel using a mixture of isopropanol/H$_2$O (80/20 ratio, v/v). The most pure fractions (by HPLC) were combined together and concentrated in vacuo. Thus, the title compound (1.1 g, 52%) was obtained as a light yellow powder. HPLC purity (peak area percent): 99%. MS/MS and $^1$H NMR conformed to the desired structure.

Less pure fractions (by HPLC) were combined together and concentrated in vacuo, and ca. another 1.0 g (48% yield) of the title compound was obtained. HPLC purity (peak area percent): 96.7%. MS/MS and $^1$H NMR conformed to the desired structure.

HPLC conditions are the same as in section 7A above; Retention time of H-D-iGlu-D-Trp-OH is 4.0 min.

EXAMPLE 8

A. Preparation of H-D-Pyr-D-Trp-OH (5-oxo-D-prolyl-D-tryptophan) from Z-D-Glu-(γ-OEt)-OH The titled compound is a possible synthetic impurity of H-D-iGlu-D-Trp-OH. It is independently synthesized and used as a reference in the HPLC analysis of products described in Examples 3 to 7 above.

To an ice-cooled solution of Z-D-Glu-(γ-OEt)-OH (1 g, 3.23 mmol) in DMF (60 mL), was added N-hydroxysuccinimide (409 mg, 3.56 mmol), EDCI (682 mg, 3.56 mmol), and the resulting solution was stirred at ice-water bath for 1 h and then RT for overnight. To this reaction mixture was added H-D-Trp-OH (792 mg, 3.88 mmol) and Et$_3$N (1 mL) at RT. Water was added after 1.5 h at ice bath temperature. The mixture was extracted with EtOAc several times. The combined EtOAc extracts was washed with 10% citric acid, followed by brine, dried over Na$_2$SO$_4$, filtered, concentrated to dryness, and dried under vacuum to afford 410 mg of crude product fraction A. The aqueous layer was concentrated in vacuo at a bath temperature of 55° C. The residue was dissolved in CH$_2$Cl$_2$, and the organic fraction was washed with 10% citric acid (1×20 mL) and brine, dried over Na$_2$SO$_4$, filtered, concentrated to almost dryness at 50° C. to give crude product fraction B. Both crude product fractions A and B were combined and hydrogenated over 10% Pd/C (40% w/w of Pd/C) under atmospheric pressure using a hydrogen-filled balloon at room temperature for 2.75 hours. The reaction mixture was filtered through CELITE®. The filtrate contained the product H-D-iGlu(γ-OEt)-D-Trp-OH, and was analyzed by HPLC (same method as the one described in 7A above). The product peak has a retention time of 4.54 min. The filtrate was concentrated to dryness under reduced pressure at a bath temperature of ca. 45° C. HPLC analysis showed the partial conversion of the product with R$_t$ at 4.54 min to another peak with R$_t$ at 4.45 min. The crude product was purified by flash column chromatography using isopropanol and conc. NH₄OH (elution gradient: 90/10 to 80/20, v/v). HPLC analysis of this material (670 mg) showed a peak with $R_t$ at 4.45 min. Structure elucidation by $^1$H NMR spectroscopy indicated that the product after workup was the cyclized compound shown below:

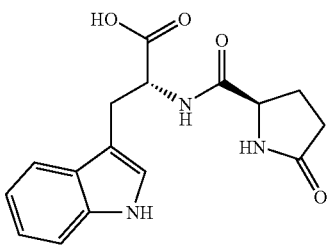

$^1$H NMR (CD₃OD) δ ppm: 7.60 (d, J=7.8 Hz, 1H), 7.31 (d, J=8.0 Hz, 1H), 7.10 (s, 1H), 7.07 (t, J=7.8 Hz, 1H), 7.00 (t, J=7.4 Hz, 1H), 4.68-4.65 (m, 1H), 4.05-4.02 (m, 1H), 3.44 (dd, J=14.6 Hz, J=4.6 Hz, 1H), 3.23-3.18 (m, 1H), 2.34-2.24 (m, 1H), 2.13-2.05 (m, 1H), 2.00-1.92 (m, 1H) and 1.76-1.68 (m, 1H). MS (m/z): 316 [M+1]⁺, 188 (100%).

$^{13}$C NMR (CD₃OD) δ ppm: 181.6, 177.5, 174.2, 138.0, 129.3, 124.5, 122.4, 119.8, 119.5, 112.3, 111.7, 58.3, 56.3, 30.2, 28.8 and 26.5.

HPLC Method: Column—Symmetry C18, 5 μm, 3.9×150 mm, WAT 046980; Mobile phase −0.035% HClO₄/CH₃CN, gradient; Method: min-CH₃CN %: 0-10%, 10-100%, 12-100%, 14-50%; Flow rate: 1.0 mL/min; Detection λ: 254 nm.

B. Independent synthesis of 5-oxo-D-prolyl-D-tryptophan from (R)(+)-2-pyrrolidine-2-5-carboxylic acid (H-D-Pyr-D-Trp-OH)

(R)(+)-2-Pyrrolidine-2,5-carboxylic acid (2.09 g, 0.016 mol) was added to 250 ml of dichloromethane. Diisopropylethylamine (3.12 ml, 0.018 mol) was added, and the solution was clear at this point. Hydroxybenzotriazole hydrate (HOBt.H₂O, 2.48 g, 0.016 mol) was added at 0° C. EDCI (4.64 g, 0.025 mol) was added. After 30 min., H-D-Trp-OBzl.HCl (4.76 g, 0.016 mol) was added, followed by diisopropylethylamine (3.12 ml, 0.018 mol). The solution was clear in 5 min and was left stirring for 16 hr. The solvent was evaporated to dryness and the material was partitioned between ethyl acetate and 10% hydrochloric acid. The ethyl acetate layer was washed with 10% sodium bicarbonate solution and then brine. The organic layer was dried over sodium sulphate and evaporated to give a foamy solid. This solid is benzyl 5-oxo-D-prolyl-D-tryptophanate. Without purification, a sample of the crude benzyl 5-oxo-D-prolyl-D-tryptophanate (1.55 g) was dissolved in methanol (30 ml) and hydrogenated over 10% Pd/C at 45 psi hydrogen for 2 hr. The catalyst was filtered through Celite and the filtrate was evaporated to give a red foam. This material was purified by column chromatography (elution gradient: 10% methanol: dichloromethane, then 50% isopropanol in dichloromethane) to give a solid (419 mg). The purity of the material can be monitored by TLC (30% aq. ammonia: isopropanol). This material is 5-oxo-D-prolyl-D-tryptophan with the same NMR data as the material in section A.

EXAMPLE 9

Synthesis of L-isoglutamyl-L-tryptophan, Mono Ammonium Salt (1:1)

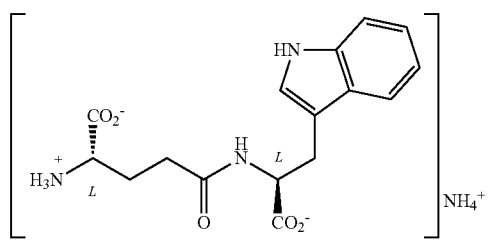

A: Synthesis of Boc-L-Glu-(γ-L-Trp-O-t-Bu)-α-O-t-Bu

A solution of Boc-L-Glu-O-t-Bu (1.50 g, 4.9 mmol) in CH₂Cl₂ (50 mL) was cooled to −3° C., and stirred for 15 min. Then, 1-hydroxybenzotriazole (HOBt, 1.00 g, 7.4 mmol), N-(3-dimethylaminopropyl)-N'-ethylcarbodiimide hydrochloride (EDC, 1.42 g, 7.4 mmol) and diisopropylethylamine (DIPEA, 1.30 mL, 7.4 mmol) were successively added. Afterwards, a solution of H-L-Trp-O-t-Bu.HCl (2.20 g, 7.4 mmol) and DIPEA (1.30 mL, 7.4 mmol) in CH₂Cl₂ (20 mL) was added dropwise. The resulting mixture was stirred at ice-cold temperature (−3° C. to 0° C.) for 1 h, then allowed to warm to room temperature, and stirred for overnight under a blanket of nitrogen.

The reaction mixture was evaporated to dryness. The residue was partitioned between EtOAc (40 mL) and a saturated solution of NaHCO₃ (100 mL). The organic fraction was collected, washed with 10% citric acid, followed by brine (30 mL). The organic layer was dried over Na₂SO₄, filtered and concentrated to a thick oil. Purification of the residue by column chromatography on silica gel using a solvent gradient of a mixture of hexanes and EtOAc (85/15, 80/20 and 60/40 ratio, v/v) as eluant afforded the title product (2.55 g, 95%) as a white solid. $^1$H NMR (DMSO-d₆) δ ppm: 10.84 (s, 1H), 8.18 (d, J=7.5 Hz, 1H), 7.52 (d, J=7.7 Hz, 1H), 7.35 (d, J=8.0 Hz, 1H), 7.12-7.15 (m, 2H), 7.06 (t, J=7.6 Hz, 1H), 6.98 (t, J=6.8 Hz, 1H), 4.41 (q, J=6.7 Hz, 1H), 3.73-3.80 (m, 1H), 2.94-3.12 (m, 2H), 2.13-2.21 (m, 2H), 1.60-1.85 (m, 2H), 1.28-1.38 (m, 27H); $^{13}$C NMR (DMSO-d₆) δ ppm: 171.5 (C), 171.4 (C), 171.1 (C), 155.5 (C), 136.1 (C), 127.2 (C), 123.5 (CH), 120.9 (CH), 118.3 (CH), 118.1 (CH), 111.3 (CH), 109.7, 80.2, 78.0, 53.9 (CH), 53.6 (CH), 31.5 (CH₂), 28.2 (CH₃), 27.9 (CH₃), 27.6 (CH₃), 27.5 (CH₃), 27.2 (CH₂), 26.6 (CH₂); MS (m/z) 546 [M+1]⁺; Anal. Calcd. for C₂₉H₄₃N₃O₇.0.5H₂O: C, 62.80; H, 8.00; N, 7.58; Found: C, 62.69; H, 8.56; N, 7.57.

B: Synthesis of L-isoglutamyl-L-tryptophan, Mono Ammonium Salt (1:1)

HCl gas was bubbled into a stirred ice-cooled (0° C. to 5° C.) solution of Boc-L-Glu-((-L-Trp-O-t-Bu)-γ-O-t-Bu obtained as described above (2.38 g, 4.4 mmol) in CH₂Cl₂ (40 mL) for 5 h. The reaction mixture became cloudy during HCl gas bubbling. The temperature of the reaction was kept at below 30° C. with ice cooling. The reaction mixture was then evaporated to afford a white solid (crude material weight=2.80 g).

Purification of a crude sample (482 mg) using reversed phase high performance flash chromatography (HPFC™)

(Biotage) with a C18HS M+40 column and a solvent gradient of a mixture of 15 mM NH$_4$OAc and CH$_3$CN as eluant afforded the title compound after solvent evaporation and freeze-drying the material (150 mg). $^1$H NMR (DMSO-d$_6$) δ ppm: 7.57 (d, J=7.8 Hz, 1H), 7.39 (d, J=8.1 Hz, 1H), 7.11-7.14 (m, 2H), 7.05 (t, J=7.2 Hz, 1H), 4.44-4.48 (m, 1H), 3.42 (t, J=5.7 Hz, 1H), 3.25 (dd, J=14.7, 4.7 Hz, 1H), 2.97-3.03 (m, 1H), 2.14-2.19 (m, 2H), 1.72-1.85 (m, 2H); FT-IR (KBr) v: 3057, 1581, 1400, 745 cm$^{-1}$; MS (m/z) 334 [diacid+1]$^+$; Anal. Calcd. for C$_{16}$H$_{22}$N$_4$O$_5$.H$_2$O: C, 52.17; H, 6.57; N, 15.21. Found: C, 51.92; H, 6.80; N, 14.94. The substance is the mono ammonium salt of L-isoglutamyl-L-tryptophan (1:1).

EXAMPLE 10

Synthesis of H-D-isoglutamyl-L-tryptophan, Mono Ammonium Salt (1:1)

A. Synthesis of Boc-D-Glu-(γ-L-Trp-O-t-Bu)-α-O-t-Bu

The procedure described in Example 1A was used. To a stirred ice-cooled solution of Boc-D-Glu-O-t-Bu (4.00 g, 13.2 mmol) in CH$_2$Cl$_2$ (75 mL) were successively added EDC (3.80 g, 19.8 mmol), HOBt (2.68 g, 19.8 mmol) and DIPEA (3.50 mL, 19.8 mmol). The resulting mixture was stirred at ice-cold temperature for 20 min. Then, a solution of H-L-Trp-O-t-Bu.HCl (5.88 g, 19.8 mmol) and DIPEA (3.50 mL, 19.8 mmol) in CH$_2$Cl$_2$ (50 mL) was added dropwise over a period of 10 min. The resulting mixture was stirred at ice-cold temperature for 1 h, then allowed to warm to room temperature, and stirred for overnight.

The reaction mixture was evaporated to dryness. The residual thick oil was taken up in EtOAc (50 mL), and the organic layer was successively washed with a saturated NaHCO$_3$ solution (100 mL), a 10% citric acid solution (100 mL), brine (100 mL), and water (100 mL). The organic layer was dried over Na$_2$SO$_4$, filtered and concentrated in vacuo. Purification of the residue by column chromatography on silica gel using a solvent gradient of a mixture of hexanes and EtOAc (8/2, 7/3 and 6/4 ratio, v/v) as eluant afforded the title product (5.88 g, 82%) as an off white solid. $^1$H NMR (DMSO-d$_6$) δ ppm: 10.85 (s, 1H), 8.18 (d, J=7.4 Hz, 1H), 7.50 (d, J=7.7 Hz, 1H), 7.33 (d, J=8.0 Hz, 1H), 7.14-7.05 (m, 3H), 6.99 (t, J=7.1 Hz, 1H), 4.40 (q, J=7.5 Hz, 1H), 3.81-3.75 (m, 1H), 3.12-3.07 (m, 1H), 3.01-2.95 (m, 1H), 2.18-2.15 (m, 2H), 1.86-1.83 (m, 1H), 1.73-1.65 (m, 1H), 1.39-1.29 (m, 27H); MS (m/z) 568 [M+Na]$^+$; 546 [M+1]$^+$; Anal. Calcd. for C$_{29}$H$_{43}$N$_3$O$_7$.0.75H$_2$O: C, 62.29; H, 8.02; N, 7.51. Found: C, 62.43; H, 7.95; N, 7.08.

B. Synthesis of H-D-Glu-(-L-Trp-OH, Mono Ammonium Salt (1:1).

The procedure described in Example 1B was used. HCl gas was bubbled into a stirred ice-cooled (about −5° C.) solution of Boc-D-Glu-(γ-L-Trp-O-t-Bu)-α-O-t-Bu obtained as described above (1.59 g, 2.91 mmol) in EtOAc (100 mL) for 45 min. The solution turned from colorless to cloudy yellow. The mixture was stirred at ice-cold temperature for 1 h, then allowed to warm to room temperature, and stirred for another 2 h. The reaction was completed as monitored by HPLC (column: Waters C18, 3.9×150 mm, WAT046980, mobile phase: solvent gradient of a mixture of 0.035% HClO$_4$ (pH=2-2.5) and acetonitrile, flow rate: 1 mL/min, δ: 210-270 nm).

The reaction mixture was concentrated under reduced pressure to a solid. The solid was dissolved in acetone, and the volatiles were removed under reduced pressure. The latter procedure was repeated two more times. Purification of the residue by column chromatography using a solvent gradient of a mixture of isopropanol and ammonium hydroxide (28-30% NH$_4$OH) (85/15 and 70/30 ratio, v/v) as eluant afforded the title product (0.42 g, 39%) as an off-white foam. Mp 120-130° C.; $^1$H NMR (D$_2$O) δ ppm: 7.67 (d, J=7.9 Hz, 1H), 7.46 (d, J=8.2 Hz, 1H), 7.18-7.22 (m, 2H), 7.13 (t, J=7.1 Hz, 1H), 4.53 (q, J=3.8 Hz, 1H), 3.45 (t, J=5.8 Hz, 1H), 3.33 (dd, J=14.7 and 4.75 Hz, 1H), 3.07 (dd, J=14.7 and 8.8 Hz, 1H), 2.19-2.31 (m, 2H), 1.78-1.98 (m, 2H); $^{13}$C NMR (D$_2$O) δ ppm: 181.4 (C), 176.6 (C), 176.5 (C), 138.8 (C), 129.9 (C), 126.9 (CH), 124.5 (CH), 121.9 (CH), 121.4 (CH), 114.5 (CH), 113.2 (C), 58.6 (CH), 56.7 (CH), 34.2 (CH$_2$), 30.3 (CH$_2$), 28.9 (CH$_2$); MS (m/z) 334 [Diacid+1]$^+$.

EXAMPLE 11

Synthesis of L-isoglutamyl-D-tryptophan, Mono Ammonium Salt (1:1)

A. Synthesis of Boc-L-Glu-((-D-Trp-OMe)-α-O-t-Bu

The procedure as described in Example 1A was used. To a stirred ice-cooled solution of Boc-L-Glu-O-t-Bu (3.45 g, 11.4 mmol) in CH$_2$Cl$_2$ (120 mL) were successively added EDC (3.31 g, 17.3 mmol), HOBt (2.36 g, 17.5 mmol) and DIPEA (3.0 mL, 17.1 mmol). The resulting mixture was stirred at ice-cold temperature for another 25 min. A solution of H-D-Trp-OMe.HCl (2.20 g, 7.40 mmol) and DIPEA (3.0 mL, 17.1 mmol) in CH$_2$Cl$_2$ (40 mL) was then added. The resulting mixture was stirred at ice-cold temperature for 1 h, then allowed to warm to room temperature, and stirred for overnight.

After usual work-up as described in Example 1A, purification of the residue by column chromatography using a solvent gradient of a mixture of hexanes and EtOAc (8/2 and 6/4 ratio, v/v) as eluant afforded the title product (4.25 g, 74%) as a white foam. $^1$H NMR (CDCl$_3$) δ ppm: 8.64 (s, 1H), 7.53 (d, J=7.7 Hz, 1H), 7.33 (d, J=8.0 Hz, 1H), 7.15 (t, J=7.2 Hz, 1H), 7.08 (t, J=7.5 Hz, 1H), 6.98 (s, 1H), 6.61 (d, J=7.2 Hz, 1H), 5.30 (d, J=7.8 Hz, 1H), 4.92 (q, J=6.8 Hz, 1H), 4.16-4.17 (m, 1H), 3.67 (s, 3H), 3.28-3.34 (m, 2H), 2.16-2.27 (m, 2H), 2.05-2.14 (m, 1H), 1.79-1.89 (m, 1H), 1.42-1.43 (m, 18H); $^{13}$C NMR (CDCl$_3$) δ ppm: 172.6 (C), 172.1 (C), 171.6 (C), 171.3 (C), 155.9 (C), 136.3 (C), 127.7 (C), 123.2 (CH), 122.2 (CH), 119.6 (CH), 118.6 (CH), 111.5 (CH), 109.9 (C), 82.3 (C), 79.9 (C), 53.7 (CH), 53.3 (CH), 52.4 (CH), 32.6 (CH$_2$), 28.9 (CH$_2$), 28.4 (CH$_3$), 28.1 (CH$_3$), 27.7 (CH$_2$); MS (m/z) 504 [M+1]$^+$; Anal. Calcd for C$_{26}$H$_{37}$N$_3$O$_7$.0.25H$_2$O: C, 61.46; H, 7.44; N, 8.27. Found: C, 61.36; H, 7.50; N, 7.84.

B. Synthesis of Boc-L-iGlu-D-Trp-OH

To a stirred solution of Boc-L-Glu-((-D-Trp-OMe)-α-O-t-Bu (3.94 g, 7.82 mmol) in MeOH (50 mL) was added a solution of NaOH (654 mg, 16.4 mmol) in H$_2$O (20 mL). The resulting solution was stirred at room temperature overnight. 1 N NaOH solution (150 mL) was added to the reaction mixture and the aqueous material was washed with EtOAc (3×100 mL). The aqueous layer was acidified with a 3N HCl solution to pH about 2, then extracted with EtOAc (3×100 mL). The organic fractions were combined, dried over Na$_2$SO$_4$ and concentrated under reduced pressure. Purification of the residue by column chromatography on silica gel using a solvent gradient of a mixture of CH$_2$Cl$_2$ and MeOH (85/15, 70/30 ratio, v/v) as eluant afforded the title product (0.55 g, 97%) as a pink foam. $^1$H NMR (MeOD-D$_4$) δ ppm: 7.58 (d, J=7.7 Hz, 1H), 7.31 (d, J=8.0 Hz, 1H), 7.05-7.09 (m, 2H), 6.99 (t, J=7.3 Hz, 1H), 4.61-4.67 (m, 1H), 4.13 (br, 1H), 3.30-3.38 (m, 2H), 3.12-3.18 (m, 1H), 2.21-2.27 (m, 2H), 1.98-2.06 (m, 1H), 1.81-1.88 (m, 1H), 1.42 (s, 9H); $^{13}$C NMR (MeOD-d$_4$) * ppm: 158.2 (C), 138.1 (C), 129.1 (C), 124.5 (CH), 122.4 (CH), 119.9 (CH), 119.5 (CH), 112.3 (CH), 111.5 (C), 80.6 (C), 33.5 (CH$_2$), 28.9 (CH$_3$), 28.7 (CH$_2$); MS (m/z) 490 [M+1]$^+$.

C. Synthesis of H-L-iGlu-D-Trp-OH, Mono Ammonium Salt (1:1)

HCl gas was bubbled into a stirred ice-cooled (about 0° C.) solution of Boc-L-iGlu-D-Trp-OH as described above (500 mg, 1.0 mmol) in a solvent mixture of CH$_2$Cl$_2$ (20 mL) and EtOAc (10 mL) for 30 min. The reaction mixture was stirred at ice-cold temperature for 1 h. The reaction was completed, as monitored by HPLC (column: Waters C18, 3.9×150 mm, WAT046980, mobile phase: solvent gradient of a mixture of 0.035% HClO$_4$ (pH=2.0-2.5) and acetonitrile, flow rate: 1 mL/min, δ: 210-270 nm).

The reaction mixture was evaporated to dryness to a dark purple foam. Purification of the residue by column chromatography using a solvent gradient of a mixture of isopropanol and ammonium hydroxide (28-30% NH$_4$OH) (85/15 and 70/30 ratio, v/v) as eluant afforded the title product (333 mg, 88%) as an orange thick oil. $^1$H NMR (D$_2$O) δ ppm: 7.64 (d, J=7.9 Hz, 1H), 7.44 (d, J=8.0 Hz, 1H), 7.16-7.19 (m, 2H), 7.10 (t, J=7.5 Hz, 1H), 4.52 (q, J=3.7 Hz, 1H), 3.44 (t, J=6.3 Hz, 1H), 3.29-3.34 (m, 1H), 3.03-3.09 (m, 1H), 2.17-2.30 (m, 2H), 1.76-1.96 (m, 2H); $^{13}$C NMR (D$_2$O) δ ppm: 181.2 (C), 176.6 (C), 176.5 (C), 138.8 (C), 129.9 (C), 126.9 (CH), 124.5 (CH), 121.9 (CH), 121.4 (CH), 114.5 (CH), 113.1 (C), 58.5 (CH), 56.7 (CH), 51.6 (CH), 34.2 (CH$_2$), 30.2 (CH$_2$), 28.9 (CH$_2$); MS (m/z) 356 [Diacid+Na]$^+$, 334 [Diacid+1]$^+$, Anal. Calcd. for C$_{16}$H$_{22}$N$_4$O$_5$.2.35H$_2$O: C, 48.94; H, 6.85; N, 14.27. Found: C, 48.94; H, 6.64; N, 14.28.

EXAMPLE 12

HPLC Analysis of D-isoglutamyl-D-tryptophan, L-isoglutamyl-L-tryptophan, L-isoglutamyl-D-tryptophan and D-isoglutamyl-L-tryptophan The diacid of the four diastereomers are analyzed on chiral column HPLC. The D, D- and L, D-diastereoisomers are from the examples above, while the D, L-isomer is from Bachem and the L, L-isomer is from Sigma. The analysis using chiral HPLC column (Table 1) shows that the D-isoglutamyl-D-tryptophan obtained is free from the other diastereomers, namely (D, L), (L, L) and (L, D) isomers.

TABLE 1

| HPLC Analysis of H-iGlu-Trp-OH | | |
|---|---|---|
| H-iGlu-Trp-OH | Retention time (HPLC Method A) (min.) | Retention time (HPLC Method B) (min.) |
| (D, D) diastereomer | 19.32 | 3.92 |
| (D, L) diastereomer | 9.46 | 3.92 |
| (L, D) diastereomer | 13.99 | 3.87 |
| (L, L) diastereomer | 6.70 | 3.91 |

Method A:
Column: CHIROBIOTIC® TAG 5 μM, 4.6×250 mm
Mobile phase: 20 mM ammonium acetate (pH=4.1)/MeOH (80/20)
Flow rate: 0.8 mL/min
Detection λ: 222, 254, 282, 450 nm
Column Temperature: 45° C.

Method B:
Column: Symmetry C18, part no: WAT 046980
Mobile phase: HClO$_4$ (pH=2)/CH$_3$CN (85/15)
Flow rate: 1.0 mL/min
Detection λ: 210-280 nm In method A, the samples are analyzed with a chiral column. The retention times of all four diastereomers are distinctly different. In method B, the samples are analyzed with a normal reverse phase column, there is virtually no difference in the retention times of the samples. The mono ammonium salt of D-isoglutamyl-D-tryptophan disclosed in the present invention is stable after 2 years of storage. HPLC analysis by method B showed that the purity at 254 nm is 99.8%.

EXAMPLE 13

A. Preparation of H-D-Glu-(γ-D-Trp-OMe)-α-OBzl HCl salt {(2R)-Amino-(4R)-[2-(1H-indol-3-yl)-1-methoxycarbonyl-ethylcarbamoyl]-butyric acid benzyl ester hydrochloride}

In a 250-mL 3 N round bottom flask equipped with a magnetic stir bar was placed Boc-D-Glu-(γ-D-Trp-OMe)-α-OBzl (20 g, 0.037 mol) and 100 mL of dichloromethane to give a clear solution upon stirring. The solution was cooled by an ice-NaCl cooling bath to −10° C. HCl gas was bubbled into the cold solution. During the reaction the temperature was in the range of −4° C. to −10° C. The reaction was completed in about 1 hour. A white solid came out from the solution. The solid product was collected by filtration. The solid was washed with dichloromethane (40 mL×2), air-dried first, then dried in a vacuum oven at 42° C. overnight to give 16.4 g (94%, HPLC purity 98.2%). $^1$H NMR (DMSO-d$_6$) δ ppm: 10.93 (s, 1H), 8.61 (b, 3H), 8.50 (d, J=7.4 Hz, 1H), 7.47 (d, J=7.4 Hz, 1H), 7.40-7.32 (m, 6H), 7.17 (s, 1H), 7.06 (t, J=7.4 Hz, 1H), 6.97 (t, J=7.4 Hz, 1H), 5.26-5.14 (m, 2H), 4.51-4.46 (m, 1H), 4.05-3.95 (m, 1H), 3.56 (s, 3H), 3.16-3.11 (m, 1H), 3.06-3.01 (m, 1H), 2.40-2.26 (m, 2H), 2.00-1.98 (m, 2H). HPLC method: Column: XTerra MS C18 5 μm 4.6×250 mm; Mobile phase: A=the aqueous phase: 4 mM Tris, 2 mM EDTA, pH 7.4, B=the organic phase: CH$_3$CN. The gradient program: B %: 0 min. 5%, 15 min. 55%, 30 min. 55%, 32 min. 5%, 40 min. 5%. Flow rate: 1 ml/min; injection volume=5 μL; wavelength: 222, 254, 282, 450 nm. R$_t$ of the starting material=25.1 min; R$_t$ of the product=17.2 min.

B. Preparation of (2R)-Amino-(4R)-[2-(1H-indol-3-yl)-1-methoxycarbonyl-ethylcarbamoyl]-butyric acid methyl ester hydrochloride; H-D-Glu-(γ-D-Trp-OMe)-α-OMe HCl salt In a 250-mL 3 N round bottom flask equipped with a magnetic stir bar was placed Boc-D-Glu-(γ-D-Trp-OMe)-α-OMe (2.8 g, 6.06 mmol) and methanol (30 mL) to give a clear solution upon stirring. The solution was cooled by an ice-NaCl cooling bath to −12° C. HCl gas was bubbled into the cold solution. During the reaction the temperature was in the range of −12° C. to +9° C. The reaction was completed in about 30 minutes. About half of the reaction mixture was concentrated to dryness to give a solid 1.3 g (HPLC purity 96.8%). $^1$H NMR (DMSO-d$_6$) δ ppm: 10.90 (s, 1H), 8.48-8.46 (m, 4H), 7.48 (d, J=7.8 Hz, 1H), 7.34 (d, J=8.0 Hz, 1H), 7.16 (s, 1H), 7.07 (t, J=7.4 Hz, 1H), 6.98 (t, J=7.4 Hz, 1H), 4.52-4.47 (m, 1H), 4.05-3.99 (m, 1H), 3.69 (s, 3H), 3.58 (s, 3H), 3.17-3.12 (m, 1H), 3.07-3.01 (m, 1H), 2.37-2.23 (m, 2H), 1.98-1.91 (m, 2H). HPLC method: Column: XTerra MS C18 5 μm 4.6×250 mm; Mobile phase: A=the aqueous phase: 4 mM Tris, 2 mM EDTA, pH 7.4; B=the organic phase: CH$_3$CN. The gradient program: B %: 0 min. 5%, 15 min. 55%, 30 min. 55%, 32 min. 5%, 40 min. 5%. Flow rate: 1 ml/min. Injection volume=5 μL; wavelength: 222, 254, 282, 450 nm; R$_t$ of the starting material=18.7 min, R$_t$ of the product=13.0 min.

C. Preparation of H-D-Glu-(γ-D-Trp-OMe)-α-OBzl HCl salt {(2R)-Amino-(4R)-[2-(1H-indol-3-yl)-1-methoxycarbonyl-ethylcarbamoyl]-butyric acid benzyl ester hydrochloride}

A solution of HCl in ethyl acetate was prepared by bubbling HCl gas, generated by dropwise addition of 50 mL of conc HCl over conc $H_2SO_4$, into ice-cooled (0-4° C.) ethyl acetate (100 mL). This cold acid solution was placed in a dropping funnel and was added to a slight suspension of Boc-D-Glu(D-Trp-OMe)-OBzl (36.45 g, 67.80 mmol) in 150 mL of ethyl acetate. A thick suspension was obtained within 5 min. After all the HCl solution was added, HCl gas was generated as described above and bubbled into the resulting suspension directly. The internal temperature was kept at between 5-10° C. with ice cooling. The stirred suspension was maintained at 5-15° C. for 2.5 h, then allowed to warm to room temperature. The progress of the reaction was monitored by TLC (hexanes/EtOAc, 1/1, v/v as eluant). The solid was collected by suction filtration, washed with EtOAc (2×100 mL), then dried in a vacuum oven for overnight. A light pinkish solid was obtained (27.49 g, 86% yield). Analytical data were similar to those reported in Example 13A above, with the exception of some residual EtOAc which was detected by $^1$H NMR. The residual EtOAc can be removed by air-drying for 24 to 48 h prior to vacuum oven drying.

D. Preparation of H-D-Glu-(γ-D-Trp-OMe)-α-OBzl HCl salt {(2R)-Amino-(4R)-[2-(1H-indol-3-yl)-1-methoxycarbonyl-ethylcarbamoyl]-butyric acid benzyl ester hydrochloride}

In a 3 L round bottle flask was charged with Boc-D-Glu-OBzl (200.0 g, 0.593 mol) and EtOAc (1.6 L). Diisopropylethylamine (206.5 mL, 1.186 mol)) was added to the resulting white suspension. The internal temperature was about 21° C., and a thick suspension was observed. The suspension gradually thinned and dissolved within 15 min to give a clear solution. Then N-(3-Dimethylaminopropyl)-N'-ethylcarbodiimide hydrochloride (136.4 g EDC, 0.711 mol) was added as a suspension formed. HCl.H-D-TrpOMe (166.1 g, 0.652 mol) was added portionwise over 30 min. An exotherm was observed as the internal temperature reached 28° C. After 2 hr, the internal temperature dropped to 25° C. The resulting suspension was vigorously stirred for overnight at room temperature. The reaction mixture was diluted with EtOAc (200 mL), then successively washed with 1 N HCl (600 mL) and with a 5% HCl solution (2×256 mL). A sample of the crude mixture was concentrated and analyzed by TLC and $^1$H NMR. The water content by Karl-Fisher test was 2.3%.

The contents of the flask were cooled in an ice-bath, and the internal temperature was about 0° C. HCl gas was bubbled into the ice-cooled solution for 1 h. An exotherm was observed within 10 min after bubbling HCl gas, and the internal temperature reached about 19° C. After 20 min of bubbling, the internal temperature was 22° C. The resulting suspension was stirred for another hour. The solid was collected by suction filtration and washed with EtOAc (2×640 mL) then dried under vacuum to a constant weight (243.8 g). Analytical data were similar to those reported in Example 13A above. The presence of EtOAc (about 10% by proton integration) was also observed by $^1$H NMR. The trapped EtOAc could be removed by air-drying the solid for 24-48 h prior to oven drying.

EXAMPLE 14

Preparation of a Solution of the Base Addition Salt of D-isoglutamyl-D-tryptophan and its Conversion to Thymodepressin D-isoglutamyl-D-tryptophan Procedure 14A:

The starting material H-D-Glu-(γ-D-Trp-OMe)-α-OBzl HCl salt (4.0 g, 8.4 mmol) was placed in a 250 mL 3 N round bottom flask equipped with a magnetic stir bar. Methanol (20 mL) was added to give a clear solution. The solution was cooled by an ice-NaCl salt bath to −10° C. A NaOH solution (3 N, 8.4 mL, 25.2 mmol) was added. HPLC was used to monitor the reaction. After 2 hours the HPLC analysis of the reaction mixture indicated that the reaction was not completed yet. A NaOH solution (3 N, 1.4 mL, 4.2 mmol) was added. At this point, a total of 29.4 mmol of NaOH was added. After another 4 hours the HPLC analysis of the reaction mixture indicated that the product in the reaction mixture was higher than 95.2%. The reaction was stopped. The reaction mixture was acidified, under cooling using an ice-water bath, to pH 6.5 by adding hydrochloric acid (6 N, ~1.3 mL, 7.8 mmol). The resulting solution was concentrated to remove most of methanol to a volume of 15 mL. The solution was washed with ethyl acetate (15 mL×2). The solution was filtered to collect the filtrate. The filtrate was further acidified to pH 3 by adding hydrochloric acid (6N, ~1.3 mL, 7.8 mmol). At this point, a total of ~15.6 mmol of hydrochloric acid was used. A solid formed upon stirring at room temperature. The mixture was stirred overnight. The solid was collected by filtration. The solid was air-dried to get a crude product 2.4 g. The solid then put back to a round bottom flask. Deionized water (15 mL) was added, and the mixture was stirred for 2 hours. The solid was collected by filtration. The solid was air-dried again, and then put back to a round bottom flask again. Deionized water (15 mL) was added, and the mixture was stirred for 1 hour. The solid was collected by filtration, and washed with ice-cold deionized water (6 mL×3). The solid was proven to be chloride free by silver nitrate test. The solid was air-dried, then put into the vacuum oven at 42° C. for 19 hours to give 1.3 g (46%, HPLC purity 98.8%). The filtrates and water washing solutions were combined and concentrated for the isolation of a second crop of product. $^1$H NMR ($D_2O$—NaOD pH 7.0) δ ppm: 7.59 (d, J=7.6 Hz, 1H), 7.38 (d, J=7.6 Hz, 1H), 7.15-7.12 (m, 2H), 7.05 (t, J=7.2 Hz, 1H), 4.47-4.44 (m, 1H), 3.40 (t, J=6.1 Hz, 1H), 3.30-3.25 (m, 1H), 3.03-2.97 (m, 1H), 2.3-2.1 (m, 2H), 1.84-1.69 (m, 2H). MS (m/z) 334.3 [M+1]$^+$. HPLC method: Column: XTerra MS C18 5 µm 4.6×250 mm. Mobile phase: A=the aqueous phase: 4 mM Tris, 2 mM EDTA, pH 7.4; B=the organic phase: $CH_3CN$. The gradient program: B %: 0 min. 5%, 15 min. 55%, 30 min. 55%, 32 min. 5%, 40 min. 5%. Flow Rate: 1 ml/min. Injection volume=5 µL. Wavelength: 222, 254, 282, 450 nm. $R_t$ of the product=6.5 min.

Procedure 14B:

Lithium hydroxide monohydrate (0.374 g, 8.9 mmol) was dissolved in 3.5 mL of deionized water. The solution was placed in a 100 mL 1 N round bottom flask equipped with a magnetic stir bar. 6.5 mL of methyl tert-butyl ether was added to the solution. At room temperature the starting material H-D-Glu-(γ-D-Trp-OMe)-α-OBzl HCl salt (2.0 g, 4.2 mmol) was added to form a suspension. Methanol (2 mL) was added, most of the solid dissolved. HPLC was used to monitor the reaction. There was still starting material in the reaction mixture after stirring at room temperature overnight. Lithium hydroxide monohydrate (0.190 g, 4.5 mmol) was dissolved in 2 mL of deionized water, and added to the reaction mixture followed by addition of 2 mL of methanol. At this point, a total of 13.4 mmol of LiOH was added. After 4 hours the HPLC analysis of the reaction mixture indicated that the reaction was not completed yet. Lithium hydroxide monohydrate (0.100 g, 2.4 mmol) was dissolved in 1 mL of deionized water, and added to the reaction mixture. At this point, a total of 15.8 mmol of LiOH was added. After another 2.5 hours the HPLC analysis of the reaction mixture indicated that the product in the reaction mixture was higher than 97.5%. The reaction was stopped. The reaction mixture was poured into a separatory funnel and the 2 phases separated. The aqueous phase was washed with ethyl acetate (15 mL×2). The aqueous phase was acidified, under cooling using an ice-water bath, to pH 6 by adding hydrochloric acid (6 N, ~650 µL, 3.9 mmol). The aqueous phase was concentrated to 5 mL, and filtered to collect the filtrate. The filtrate was further acidified to pH 3 by adding hydrochloric acid (6 N, ~700 µL, 4.2 mmol). At this point, a total of ~8.1 mmol of hydrochloric acid was used. A solid formed upon stirring at room temperature. The solid was collected by filtration. The solid was air-dried, then put back to a round bottom flask. Deionized water (6 mL) was added, and the mixture was stirred for 15 minutes. The solid was collected by filtration, and washed with ice-cold deionized water (6 mL×6). The solid was proven to be chloride free by silver nitrate test. The solid was air-dried, then put into the vacuum oven at 42° C. for 12 hours to give 0.44 g (31%, HPLC purity 98.5%). The filtrates and water washing solutions were combined and concentrated for further isolation of a second crop of the product. $^1$H NMR (D$_2$O—NaOD pH 6.0) δ ppm: 7.59 (d, J=7.7 Hz, 1H), 7.38 (d, J=7.7 Hz, 1H), 7.15-7.12 (m, 2H), 7.05 (t, J=7.2 Hz, 1H), 4.47-4.44 (m, 1H), 3.41 (t, J=6.0 Hz, 1H), 3.29-3.25 (m, 1H), 3.03-2.97 (m, 1H), 2.3-2.1 (m, 2H), 1.83-1.58 (m, 2H).

HPLC method: Column: XTerra MS C18 5 µm 4.6×250 mm. Mobile phase: A=the aqueous phase: 4 mM Tris, 2 mM EDTA, pH 7.4; B=the organic phase: CH$_3$CN. The gradient program: B %: 0 min. 5%, 15 min. 55%, 30 min. 55%, 32 min. 5%, 40 min. 5%.

1 ml/min. Injection volume=5 µL. Wavelength: 222, 254, 282, 450 nm. R$_t$ of the product=6.5 min.

Thymodepressin prepared in the present invention has a water solubility of from about 20 to about 23 mg per ml in water. The water washing in Procedures A & B serves to remove inorganic salts such as sodium chloride or lithium chloride. In large scale preparation, the volume of aqueous washing can be controlled by computing the amount of inorganic salt present and using the solubility to determine the amount of water required to wash the product.

As many changes can be made to the preferred embodiments of the present invention without departing from the scope of the present invention, it is intended that all material contained herein be interpreted as illustrative of the present invention and not in a limiting sense.

The invention claimed is:

1. Crystalline D-isoglutamyl-D-tryptophan characterized by the X-ray powder diffraction pattern as illustrated in FIG. 1.

2. Crystalline D-isoglutamyl-D-tryptophan characterized by the following X-ray powder diffraction pattern expressed in terms of inter-planar distances d, Bragg's angle 2 theta, and relative intensity (expressed as a percentage with respect to the most intense ray):

| Angle [°2 theta] | d-value [Å] | Rel. Int [%] |
| --- | --- | --- |
| 6.67 | 13.239 | 3 |
| 11.09 | 7.975 | 4.4 |
| 11.77 | 7.515 | 1.2 |
| 13.29 | 6.655 | 4 |
| 14.26 | 6.205 | 11.3 |
| 15.58 | 5.685 | 33.3 |
| 16.81 | 5.269 | 28.9 |
| 17.27 | 5.13 | 30.4 |
| 18.35 | 4.832 | 12.2 |
| 18.87 | 4.7 | 95.8 |
| 20.05 | 4.424 | 63.6 |
| 20.9 | 4.247 | 33.2 |
| 22.03 | 4.032 | 17.1 |
| 22.88 | 3.884 | 100 |
| 23.74 | 3.744 | 97.9 |
| 24.54 | 3.625 | 41.9 |
| 25.44 | 3.499 | 20.3 |
| 25.69 | 3.465 | 12.1 |
| 26.31 | 3.384 | 16.4 |
| 27 | 3.3 | 27.4 |
| 27.75 | 3.212 | 24.9 |
| 28.18 | 3.164 | 19.3 |
| 28.79 | 3.099 | 6.8 |
| 29.13 | 3.063 | 6.2 |
| 29.91 | 2.985 | 79.2 |
| 31.04 | 2.879 | 8.6 |
| 31.49 | 2.839 | 33.7 |
| 32.54 | 2.749 | 4.4 |
| 33.29 | 2.689 | 9.3 |
| 33.97 | 2.637 | 10.5 |
| 34.99 | 2.562 | 17.3 |
| 35.54 | 2.524 | 21.8 |
| 36.14 | 2.483 | 5.1 |
| 36.74 | 2.444 | 5.9 |
| 37.35 | 2.406 | 7.7 |
| 38.31 | 2.348 | 25.6 |
| 39.01 | 2.307 | 20.3 |

3. A pharmaceutical composition comprising the crystalline salt of the compound of claim 1 and at least one pharmaceutically acceptable excipient.

4. A method of treatment of psoriasis comprising administering an effective amount of the crystalline compound of claim 1 to a subject in need thereof.

5. A pharmaceutical composition comprising the crystalline salt of the compound of claim 2 and at least one pharmaceutically acceptable excipient.

6. A method of treatment of psoriasis comprising administering an effective amount of the crystalline compound of claim 2 to a subject in need thereof.

* * * * *